US010065976B2

(12) United States Patent
Tonks et al.

(10) Patent No.: US 10,065,976 B2
(45) Date of Patent: Sep. 4, 2018

(54) TITANIUM (IV) COMPOUNDS AND METHODS OF FORMING HETEROCYCLIC COMPOUNDS USING SAME

(71) Applicant: REGENTS OF THE UNIVERSITY OF MINNESOTA, Minneapolis, MN (US)

(72) Inventors: Ian A. Tonks, Minneapolis, MN (US); Zachary W. Gilbert, Minneapolis, MN (US)

(73) Assignee: REGENTS OF THE UNIVERSITY OF MINNESOTA, Minnepolis, MN (US)

( * ) Notice: Subject to any disclaimer, the term of this patent is extended or adjusted under 35 U.S.C. 154(b) by 57 days.

(21) Appl. No.: 14/986,928

(22) Filed: Jan. 4, 2016

(65) Prior Publication Data

US 2016/0200746 A1  Jul. 14, 2016
US 2017/0158718 A9  Jun. 8, 2017

Related U.S. Application Data

(60) Provisional application No. 62/102,173, filed on Jan. 12, 2015.

(51) Int. Cl.
| | |
|---|---|
| C07F 7/28 | (2006.01) |
| B01J 31/18 | (2006.01) |
| C07D 207/333 | (2006.01) |
| C07D 207/323 | (2006.01) |
| C07D 209/52 | (2006.01) |
| C07D 209/44 | (2006.01) |
| C07F 7/08 | (2006.01) |

(52) U.S. Cl.
CPC ............ *C07F 7/28* (2013.01); *B01J 31/1805* (2013.01); *C07D 207/323* (2013.01); *C07D 207/333* (2013.01); *C07D 209/44* (2013.01); *C07D 209/52* (2013.01); *C07F 7/0814* (2013.01); *B01J 2231/321* (2013.01); *B01J 2231/324* (2013.01); *B01J 2531/46* (2013.01)

(58) Field of Classification Search
CPC .... C07F 7/28; B01J 31/1805; C07D 207/323; C07D 207/333; C07D 209/44; C07D 209/52
See application file for complete search history.

(56) References Cited

U.S. PATENT DOCUMENTS 6,861,559 B2  3/2005  Odom

OTHER PUBLICATIONS

Al-Masoudi et al. "1,2,4-Triazoles: Synthetic Approached and Pharmacological Importance. (Review)" Chemistry of Heterocyclic Compounds, 2006, vol. 42, pp. 1377-1403.*
Ackermann, "TiCl4-Catalyzed Intermolecular Hydroamination Reactions of Norbornene" 2004 *Org. Let.*, 6:2515-2518.
Adams, "New titanium imido synthons: syntheses and supramolecular Structures" 2005 *Inorg. Chem.* 44:2882-2894.
Agapie, "Zirconium and Titanium Complexes Supported by Tridentate LX2 Ligands Having Two Phenolates Linked to Furan, Thiophene, and Pyridine Donors: Precatalysts for Propylene Polymerization and Oligomerization" Nov. 2008 *Organometallics*, 27(23):6245-6256.
Al Dulayymi, "A simple and efficient hydrodehalogenation of 1,1-dihalocyclopropanes" 1996 *Tet. Let.* 37: 8933-8936.
Albertin, "Preparation of Benzyl Azide Complexes of Iridium(III)" Dec. 2007 *Inorg. Chem.*, 47(2):742-748.
Amatore, Highly Enantioselective Rhodium-Catalyzed [2+2+2] Cycloaddition of Diynes to Sulfonimines. 2013 *J. Am. Chem. Soc.* 135, 4576-4579.
Aneetha, "Ti(NMe2)4 and [HNMe2Ph][B(C6F5)4]: A Convenient Blend for Effective Catalytic Carboamination of Alkynes" Apr. 2006 *Organometallics*, 25(10):2402-2404.
Bandlish, Substituent effects in radical reactions. III. Thermolysis of substituted phenylazomethanes, 3,5-diphenyl-1-pyrazolines, and azopropanes. 1975 *J. Am. Chem. Soc.* 20, 5856-5862.
Baranger, "Variable regiochemistry in the stoichiometric and catalytic hydroamination of alkynes by imidozirconium complexes caused by an unusual dependence of the rate law on alkyne structure and temperature" 1993 *J. Am. Chem. Soc.*, 115:2753-2763.
Barden, "Indoles: Industrial, Agricultural and Over-the-Counter Uses" Jul. 2010 *Top Hetrocycl. Chem.*, 26:31-46.
Basuli, "Understanding the role of an easy-to-prepare aldimine-alkyne carboamination catalyst, [Ti(NMe2)3(NHMe2)][B(C6F5)4]" 2011 *J. Orgomet. Chem.*, 696:235-243.
Baumann, "An overview of the key routes to the best selling 5-membered ring heterocyclic pharmaceuticals" 2011 *Beilstein J. Org. Chem.*, 7:442-495.
Benzing, "Dialkylamido-titan(IV)-chloride and -alkoholate" Aug. 1961 *Chem. Ber.*, 94:2263-2267.
Biswal, "Indole: The Molecule of Diverse Biological Activities" 2012 *Asian J. Pharm. and Clinical Research*, 5(1):1-6.
Blake, "Synthesis and imido-group exchange reactions of tert-butylimidotitanium complexes" 1997 *J. Chem. Soc. Dalton Trans.*, 1539-1558.
Blanco-Urgoiti, "The Pauson-Khand reaction, a powerful synthetic tool for the synthesis of complex molecules" 2004 *Chem. Soc. Rev.*, 33:32-42.
Bodkin, "The Sharpless asymmetric aminohydroxylation" 2002 *J. Chem. Soc. Perkin Trans. 1*, 24:2733-2746.
Bradley, "Metallo-organic compounds containing metalnitrogen bonds. Part I. Some dialkylamino-derivatives of titanium zirconium" 1960 *J. Chem. Soc.* 3857-3861.
Broere, "Recent Advances in Transition-Metal-Catalyzed [2+2+2]-Cyclo(co)trimerization Reactions" 2012 *Synthesis* 44(17):2639-2672.
Bullock, "*Catalysis without precious metals*" Wiley, 2010. Title page, copyright page, Table of Contents.
Chopade, "[2+2+2] Cycloaddition reactions catalyzed by transition metals" 2006 *Adv. Synth. Cataly.* 348, 2307-2327.

(Continued)

*Primary Examiner* — Joseph R Kosack
(74) *Attorney, Agent, or Firm* — Mueting, Raasch & Gebhardt, PA

(57) ABSTRACT

The present disclosure provides Titanium (IV) compounds and methods of making heterocyclic compounds such as pyrroles using Titanium (IV) compounds. In certain embodiments, the Titanium (IV) compound is present in catalytic amounts.

16 Claims, 11 Drawing Sheets

(56) References Cited

OTHER PUBLICATIONS

Coles, "Exploration of the Suitability of Bicyclic Guanidinates as Ligands in Catalytic Chemistry Mediated by Titanium" Nov. 2003 *Organometallics*, 22(25)5201-5211.

Dias, "Copper and Silver Complexes Containing Organic Azide Ligands: Syntheses, Structures, and Theoretical Investigation of [HB(3,5-(CF3)2Pz)3]CuNNN(1-Ad) and [HB(3,5-(CF3)2Pz)3]AgN(1-Ad)NN (Where Pz=Pyrazolyl and 1-Ad=1-Adamantyl)" Aug. 2000 *Inorg. Chem.*, 39(17):3894-3901.

Díaz-Requejo, "Coinage metal catalyzed C—H bond functionalization of hydrocarbons" 2008 *Chem. Rev.* 108, 3379-3394.

Dick, "Transition metal catalyzed oxidative functionalization of carbon-hydrogen bonds" 2006 *Tetrahedron*62, 2439-2463.

Driver, "Recent advances in transition metal-catalyzed N-atom transfer reactions of azides" Jul. 2010 *Org. Biomol. Chem.*, 8:3831-3846.

Duchateau, "Carbon-carbon double-bond formation in the intermolecular acetonitrile reductive coupling promoted by a mononuclear titanium(II) compound. Preparation and characterization of two titanium(IV) imido derivatives" Dec. 1991 *Inorg. Chem.*, 30(25):4863-4866.

Durfee, "Formation and characterization of .eta.2-imine and .eta.2-azobenzene derivatives of titanium containing ancillary aryloxide ligation" Jan. 1990 *Organometallics*, 9(1):75-80.

Estévez, "Recent advances in the synthesis of pyrroles by multicomponent reactions" 2014 *Chem. Soc. Rev.*, 43:4633-4657 (2014).

Fang, "Reactions of substituted (1,3-Butadiene-1,4-diyl)magnesium, 1,4 bis(bromomagnesio)butadienes and 1,4-dilithiobutadienes with ketones, aldehydes and PhNO to yield cyclopentadiene derivatives and N-Ph pyrroles by cyclodialkenylation" 2004 *Chem. Eur. J.* 10:3444-3450.

Feng, "Aggregation-induced emission enhancement of aryl-substituted pyrrole derivatives" 2010 *J. Phys. Chem. B* 50:16731-16736.

Ferreira, "Recent advances in the synthesis of pyrroles" Oct. 2001 *Org. Prep. Proced. Int.*, 33(5):411-454.

Fickes, "Isolation and Structural Characterization of the Terminal Mesityl Azide Complex V(N3Mes)(I)(NRArF)2 and Its Conversion to a Vanadium(V) Imido Complex" Jun. 1995 *J. Am. Chem. Soc.*, 117(23):6384-6385.

Focht "Azo-complexes of bis(cyclopentadienyl)-titanium and -vanadium; model systems for N—N multiple bond activation" 1983 *J Chem. Soc. Dalton Trans.*, 1515-1521.

Fout, "The recent progression of synthetic strategies to assemble titanium complexes bearing the terminal imide group" 2007 *Chem. Eur. J.*, 13:9428-9440.

Franzen, "Recent Advances in the Preparation of Heterocycles on Solid Support: A Review of the Literature" May 2000 *J. of Comb. Chem.*, 2(3):195-214.

Gehrmann, "Synthesis, Characterization, and Thermal Rearrangement of Zirconium Tetraazadienyl and Pentaazadienyl Complexes" Jun. 2012 *Organometallics*, 31(12):4504-4515.

Gilbert, "Catalytic formal [2+2+1] synthesis of pyrroles from alkynes and diazenes via TiII/TiIV redox catalysis" Nov. 2, 2015 *Nature Chemistry*, online, 6 pages. DOI: 10.1038/NCHEM.2386.

Gilbert, "Catalytic formal [2+2+1] synthesis of pyrroles from alkynes and diazenes via TiII/TiIV redox catalysis [Supplementary Information]" *Nature Chemistry*, online, 68 pages. DOI: 10.1038/NCHEM.2386.

Gray, "Alkoxido, Amido, and Imido Derivatives of Titanium(IV) Tetratolylporphyrin" 1997 *Inorg. Chem.* 36(3):278-283.

Gray, "Synthesis, electrochemistry, and imido and transfer reactions of (TTp)Ti($\eta^2$-PhN=NPh)" 1998 *Chemistry Publications, Iowa State University*, 37, 5 pages. lib.dr.iastate.edu/cgi/viewcontent.cgi?article=1744&context=chem_pubs.

Guiducci, "Reactions of Cyclopentadienyl-Amidinate Titanium Imido Compounds with CS2, COS, Isocyanates, and Other Unsaturated Organic Compounds" Feb. 2006 *Organometallics*, 25(5):1167-1187.

Gulevich, "Transition Metal-Mediated Synthesis of Monocyclic Aromatic Heterocycles (review)" 2013 *Chemical Reviews* 113:3084-3213.

Hanna, "Synthesis of a Base-Free Titanium Imido and a Transient Alkylidene from a Titanocene Dinitrogen Complex. Studies on TiNR Hydrogenation, Nitrene Group Transfer, and Comparison of 1,2-Addition Rates" Jun. 2004 *Organometallics*, 23(14):3448-3458.

Heyduk, "Designing Catalysts for Nitrene Transfer Using Early Transition Metals and Redox-Active Ligands" Jul. 2011 *Inorg. Chem.*, 50(20)9849-9863.

Hicks, "Highly enantioselective catalytic Pauson-Khand type-formation of bicyclic cyclopentenones" 1996 *J. Am. Chem. Soc.*, 188:11688-11689.

Hicks, "Scope of the intramolecular titanocene-catalyzed Pauson-Khand type reaction" 1999 *J. Am. Chem. Soc.*, 121:5881-5898.

Hill, "Synthesis, Structure, and Reactivity of Aryloxo(imido)titanium Complexes" 1990 *Angew. Chem. Int. Ed Engl.*, 102:664-665.

Hill, "Formation, fragmentation, and isomerization of titanacycle rings supported by aryloxide ligation" Aug. 1990 *Organometallics*, 9(8):2211-2213.

Hill, "Formation of a terminal aryl-imido compound of titanium by cleavage of the nitrogen-nitrogen double bond in benzo[c]cinnoline" Mar. 1991 *Inorg. Chem.*, 301(5)1143-1144.

Johnson, "Imidotitanium Complexes as Hydroamination Catalysts: Substantially Enhanced Reactivity from an Unexpected Cyclopentadienide/Amide Ligand Exchange" Mar. 2001 *J. Am. Chem. Soc.*, 123(12):2923-2924.

Kaleta, "Reactions of group 4 metallocene alkyne complexes with azobenzene: formation of diazametallacyclopropanes and N=N bond Activation" 2010 *Organometallics*, 29:2604-2609.

Kaleta, "Unusual bond activation processes in the reaction of group 4 cyclopentadienyl alkyne complexes with azobenzene" 2011 *Inorganica Chim. Acta*, 370:187-190.

Kaushik, "Biomedical Importance of Indoles" Jun. 2013 *Molecules*, 18(6):6620-6662.

Ketterer, "Imido and Organometallic-Amido Titanium(IV) Complexes of a Chelating Phenanthrenediamide Ligand" Sep. 2007 *Organometallics*, 26(22):5330-5338.

Krafft, "Effect of coordinating ligands on the Pauson-Khand cycloaddition: trapping of an intermediate" 1993 *J. Am. Chem. Soc.*, 115:7199-7207.

Krafft, "The interrupted pauson-khand reaction" 1996 *J. Am. Chem. Soc.*, 118:6080-6081.

Kulinkovich, "The chemistry of cyclopropanols" 2003 *Chem. Rev.*, 103:2597-2632.

Li, "Recent Advances in Silver-Catalyzed Nitrene, Carbene, and Silylene-Transfer Reactions" May 2006 *European J. Org. Chem.*, 2006(19):4313-4322.

Li "Nitrene Transfer Reactions Catalyzed by Gold Complexes" Jul. 2006 *Org. Chem.*, 71(16):5876-5880.

Li, One-Pot AgOAc-Mediated Synthesis of Polysubstituted Pyrroles from Primary Amines and Aldehydes: Application to the Total Synthesis of Purpurone. 2010 *Org. Lett.*, 12:4066-4069.

Liao, Copper-catalyzed double N-Vinylation of Aromatic mines: an efficient synthesis of various substituted N-Arylpyrroles. 2010 *Eur. J. Org. Chem.* 2010:5327-5508.

Liu, "One-pot silver-catalzyed and PIDA-mediated sequential reactions: synthesis of polysubstituted pyrroles directly from alkynoates and amines" 2010 *Org. Let.*, 12, 312-315.

Liu, "Chiral dienes as 'ligands' for borane-catalyzed metal-free asymmetric hydrogenation of imines" 2013 *J. Am. Chem. Soc.*, 135:6810-6813.

Lokare, "Group 6 imido activation by a ring-strained alkyne" 2004 *Organometallics*, 23:5386-5388.

Loudet, "BODIPY dyes and their derivatives: syntheses and spectroscopic studies" 2007 *Chem. Rev.*, 107:4891-4932.

Luca, "Redox-active ligands in catalysis" Sep. 2012 *Chem. Soc. Rev.*, 42:1440-1459.

Lucht, "A Zirconocene-coupling route to substituted poly(p-phenylenedienylene)s: band gap tuning via conformational control" 1998 *J. Am. Chem. Soc.*, 120:4354-4365.

(56) References Cited

OTHER PUBLICATIONS

Martin, "Cu-Catalyzed Tandem C—N Bond Formation for the Synthesis of Pyrroles and Heteroarylpyrroles" 2007 *Org. Let.*, 9:3379-3382.

McGrane, "Synthetic applications of Group IV metal-imido complex-alkyne [2+2] cycloadditions. A concise total synthesis of (.+-.)-monomorine" Feb. 1992 *Org. Chem.*, 57(5):1323-1324.

McGrane, "Intramolecular [2+2] cycloadditions of Group IV metal-imido complexes. Applications to the synthesis of dihydropyrrole and tetrahydropyridine derivatives" Jun. 1992 *J. Am. Chem. Soc.*, 114(13):5459-5460.

McGrane, "Synthetic applications of imidotitanium-alkyne [2+2] cycloadditions. A concise, stereocontrolled total synthesis of the antifungal agent (+)-preussin" Dec. 1993 *J. Am. Chem. Soc.*, 115(24):11485-11489.

Morohashi, "Highly regioselective [2+2+2] cycloaddition of terminal alkynes catalyzed by titanium complexes of p-tert-butylthiacalix[4]arene" 2006 *Tetrahedron Lett.*, 47(7):1157-1161.

Müller, "Enantioselective catalytic aziridinations and asymmetric nitrene insertion into CH bonds" 2003 *Chem. Rev.*, 103:2905-2919.

Müller, "Hydroamination: direct addition of amines to alkenes and alkynes" 2008 *Chem. Rev.*, 108:3795-3892.

Mullins, "Reactivity of a Titanium Dinitrogen Complex Supported by Guanidinate Ligands: Investigation of Solution Behavior and a Novel Rearrangement of Guanidinate Ligands" Nov. 2001 *J. Inorg. Chem.*, 40(27):6952-6963.

Munhá, "Group transfer reactions of $d^0$ transition metal complexes: redox-active ligands provide a mechanism for expanded reactivity" 2013 *Dalton Trans.*, 42:3751-3766.

Nakamoto, "Reactions of zirconacyclopentadienes with nitrosobenzene. Characterization of zirconacycle intermediates and formation of N-phenylpyrroles" 2001 *Organometallics*, 20:5515-5517.

Negishi, "Zirconium-promoted bicyclization of enynes. Effects of enyne structure" 1987 *Tet. Let.*, 28:917-920.

Nesterowicz, "Basic Properties of 4-Arylazo-Phenols and 4-Arylazo-Anisoles" 1981 *Polish J. of Chem.*, 55, 1085-1092.

Nguyen, "Catalytic nitrene transfer by a zirconium(IV) redox-active ligand complex" 2011 *Chem. Sci.*, 2:166-169.

Odom, "New C—N and C—C bond forming reactions catalyzed by titanium complexes" 2005 *Dalton Trans.*, 225-233.

Omae, "Three characteristic reactions of alkynes with metal compounds in organic synthesis" 2008 *Appl. Organometal. Chem.*, 22:149-166.

Ozerov, "Highly regioselective [2+2+2] cycloaddition of alkynes catalyzed by $\eta^6$-arene complexes of titanium supported by dimethylsilyl-bridged p-tert-butyl calix[4]arene ligand" 2000 *J. Am. Chem. Soc.*, 122:6423-6431.

Priewisch, "Efficient Preparation of Nitrosoarenes for the Synthesis of Azobenzenes" Feb. 2005 *J. Org. Chem.*, 70(6):2350-2352.

Ramanathan, "Pyrrole Syntheses Based on Titanium-Catalyzed Hydroamination of Diynes" 2004 *Organic Letters*, 17:2957-2960.

Retbøll, "MO explanation of the structures of azo-transition metal complexes" 1994 *Inorg. Chem.*, 33:6403-6405.

Roizen, "Metal-Catalyzed nitrogen-atom transfer for the oxidation of aliphatic C—H bonds" 2012 *Acc. Chem. Res.*, 45:911-922.

Rosenthal, "Five-membered metallacycles of titanium and zirconium—attractive compounds for organometallics chemistry and catalysis" 2007 *Chem. Soc. Rev.* 36, 719-728 (2007).

Schmitz, "Marine natural products: pyrrololactams from several sponges" Jan.-Feb. 1985 *J. Nat. Prod.*, 48(1):47-53.

Smolensky, "Intermolecular Hydroamination of Methylenecyclopropane Catalyzed by Group IV Metal Complexes" Jul. 2007 *Organometallics*, 26(18):4510-4527.

Stein, "Structural interpretation of heme protein resonance Raman frequencies. Preliminary normal coordinate analysis results" 1975 *J. Am. Chem. Soc.*, 97:2304-2305.

Straub, "The mechanism of hydroamination of allenes, alkynes, alkenes catalyzed by cyclopentadienyltitanium-imido complexes: a density functional study" 2001 *Angew. Chem. Int. Ed. Engl.*, 40:4632-4635.

Theilmann, "Reactions of low-valent titanocene (II) fragments with trans-4,4'-azobispyridine (RN=R, R=$C_5H_4N$): formation of tetranuclear molecular squares by trans-cis isomerization" 2009 *Organometallics* 28: 2799-2807.

Thompson, "Enone-alkyne reductive coupling: a versatile entry to substituted pyrroles" 2011 *Org. Lett.* 13:3289-3291.

Thorman, "Atom transfer reactions of (TTP)Ti(eta 2-3-hexyne): synthesis and molecular structure of trans-(TTP)Ti[OP(Oct)3]2" Jan. 2001 *Inorg. Chem.*, 40(3):499-506.

Tonks, "Titanium complexes supported by pyridinebis(phenolate) ligands: active catalysts for intermolecular hydroamination or trimerization of alkynes" 2013 *Organometallics* 32, 3451-3457.

Trogler, "Synthesis, electronic structure, and reactivity of metal-lacyclotetraazapentadienes" Dec. 1990 *Acc. Chem. Res.*, 23(12):426-431.

Vernitskaya, "Polypyrrole: a conducting polymer; its synthesis, properties, and applications" 1997 *Russ. Chem. Rev.*, 66:443-457.

Vujkovic, "Imido-alkyne coupling in titanium complexes: new insight into the alkyne hydroamination reaction" 2007 *Organometallics*, 26:5522-5534.

Vujkovic, "Insertions into Azatitanacyclobutenes: New Insights into Three-Component Coupling Reactions Involving Imidotitanium Intermediates" Apr. 2008 Organometallics, 27(11):2518-2528.

Walsh, "Generation and trapping of the diphenylhydrazido(2-) complex Cp2Zr(N2Ph2). Insertion of internal alkynes into a metal-nitrogen bond, leading to 2,3-diazametallacyclopentenes" Jan. 1990 *J. Am. Chem. Soc.*, 112(2):894-896.

Walsh, "Biological formation of pyrroles: nature's logic and enzymatic machinery" 2006 *Nat. Prod. Rep.*, 23:517-531.

Waterman, "η2-Organoazide Complexes of Nickel and Their Conversion to Terminal Imido Complexes via Dinitrogen Extrusion" Aug. 2008 *J. Am. Chem. Soc.*, 130(38):12628-12629.

Watson, "Advances in nitrogen transfer reactions involving aziridines" 2006 *Acc. Chem. Res.*, 39:194-206.

Wender, "Inspirations from nature. New reactions, therapeutic leads, and drug delivery systems" 2003 *Pure Appl. Chem.*, 75:143-155.

Yim, "Bis(amidate)bis(amido) Titanium Complex: A Regioselective Intermolecular Alkyne Hydroamination Catalyst" 2014 JACS, 79(5), pp. 2015-2028.

Yu, "Syntheses of new functionalized azobenzenes for potential molecular electronic devices" 2006 *Tetrahedron* 62:10303-10310.

Yu, "Insertion of nitriles into zirconocene 1-aza-1,3-diene complexex: chemoselective synthesis of N—H and N-substituted pyrroles" 2014 *Angew. Chem. Int. Ed.*, 53:11596-11599.

Zarkesh, "Four-electron oxidative formation of aryl diazenes using a tantalum redox-active ligand complex" 2008 *Angew. Chem. Int Ed.*, 47:4715-4718.

Zhang, "Catalytic addition of alkyne C—H, amine N—H, and phosphine P—H bonds to carbodiimides: an efficient route to propiolamidines, guanidines, and phosphaguanidines" Apr. 2008 *Org. Biomol. Chem.*, 6:1720-1730.

\* cited by examiner

TITANIUM (IV) COMPOUNDS AND METHODS OF FORMING HETEROCYCLIC COMPOUNDS USING SAME

This application claims the benefit of U.S. Provisional Application No. 62/102,173, filed Jan. 12, 2015, which is hereby incorporated by reference in its entirety.

BACKGROUND

The development of earth-abundant and nontoxic catalysts for precision chemical transformations is an endeavor of modern synthesis, and recent years have seen a large effort in replacing precious group 9 and 10 metal catalysts with their lighter base metal congeners. Complementary to this research, many synthetically practical processes that utilize earth-abundant early transition metal or lanthanide catalysts have also been developed. However, due to the oxophilic, electropositive nature of early transition metals, the majority of organometallic catalytic processes that utilize them are redox-neutral. Examples of catalytic processes that rely on early transition metal redox processes are rare and mostly limited to C—C or C—H bond forming reactions, the most notable class being Kulinkovich-type cyclopropanations. Instead of proceeding through oxidative processes, early transition metal catalyzed C—N bond forming reactions typically occur through redox-neutral alkene/alkyne hydroamination and related pathways: the only example of catalytic oxidative C—N bond formation is the utilization of a Zr complex with a redox noninnocent ligand to catalytically couple isonitriles and azides to form carbodiimides.

Polysubstituted pyrroles play a key role in pharmaceuticals, materials, dyes, and natural products, and are often challenging synthetic targets. Various heterocycles have previously been formed from early transition metallacycles, but these reactions are predominantly limited to stoichiometric reactivity.

There is a continuing need in the art for new catalysts and methods for preparing pyrroles.

SUMMARY

Pyrroles are structurally important heterocycles; however, the synthesis of polysubstituted pyrroles is often challenging. Disclosed herein is a multicomponent, Ti-catalyzed formal [2+2+1] reaction of alkynes and diazenes for the oxidative synthesis of penta- and trisubstituted pyrroles: a nitrenoid analogue to classical Pauson-Khand-type syntheses of cyclopentenones. Given the scarcity of early transition metal redox catalysis, preliminary mechanistic studies are presented. Initial stoichiometric and kinetic studies indicate that the mechanism of this reaction proceeds through a formally $Ti^{II}/Ti^{IV}$ redox catalytic cycle, wherein an azatitanacyclobutene intermediate, resulting from [2+2] alkyne+Ti imido coupling, undergoes a second alkyne insertion followed by reductive elimination to yield pyrrole and a $Ti^{II}$ species. The key component for catalytic turnover is the reoxidation of the $Ti^{II}$ species to a $Ti^{IV}$ imido via the disproportionation of an $\eta^2$diazene-$Ti^{II}$ complex.

In one aspect, the present disclosure provides a Ti(IV) compound of the formula:

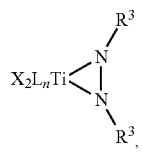

wherein: each $R^3$ independently represents an organic group, each X independently represents an anionic ligand, each L independently represents a neutral ligand, and n=2 to 3.

In another aspect, the present disclosure provides a method of forming a heterocyclic compound including: combining at least one compound having a triple bond, at least one azo compound, and at least one Ti(IV) compound under conditions effective for a [2+2+1] cycloaddition reaction to occur and form one or more heterocyclic compounds.

In some embodiments, the method includes at least one Ti(IV) compound of the formula:

wherein: each $R^3$ independently represents an organic group, each X independently represents an anionic ligand, each L independently represents a neutral ligand, and n=2 to 3. In some embodiments, the at least one azo compound is of the formula $R^3$—N=N—$R^3$, wherein each $R^3$ independently represents an organic group.

In some embodiments, the method includes at least one compound having a triple bond that is an alkyne, and the one or more heterocyclic compounds formed include one or more pyrroles.

In certain embodiments, the alkyne is of the formula $R^1$—≡—$R^2$, wherein $R^1$ and $R^2$ each independently represent H or an organic group, or $R^1$ and $R^2$ can be combined to form one or more alicyclic and/or aromatic rings; and the one or more pyrroles formed are of the formulas:

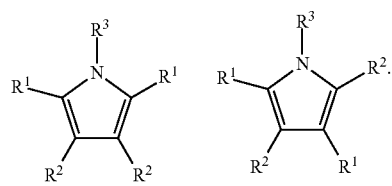

In other certain embodiments, the alkyne is of the formula $R^1$—≡—$(CH_2)_y$—≡—$R^2$, wherein $R^1$ and $R^2$ each independently represent H or an organic group, and y=3 to 5; and the one or more pyrroles formed are of the formula:

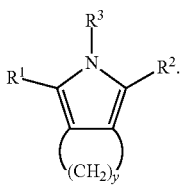

In some embodiments, the method includes at least one compound having a triple bond that is a nitrile-functional compound, and the one or more heterocyclic compounds formed include one or more triazoles.

In certain embodiments, the at least one nitrile-functional compound is of the formula $R^4$—C≡N, wherein $R^4$ represents an organic group; and the one or more triazoles formed are of the formulas:

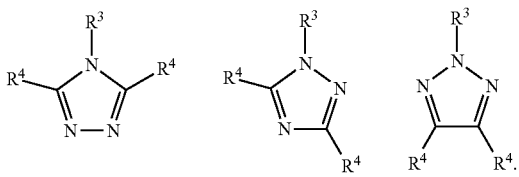

In some embodiments, the method includes at least two compounds having a triple bond including at least one alkyne and at least one nitrile-functional compound, and the one or more heterocyclic compounds formed include one or more pyrazoles and/or imidazoles.

In certain embodiments, the at least one alkyne is of the formula $R^1$—≡—$R^2$, wherein $R^1$ and $R^2$ each independently represent H or an organic group, or $R^1$ and $R^2$ can be combined to form one or more alicyclic and/or aromatic rings; the at least one nitrile-functional compound is of the formula $R^4$—C≡N, wherein $R^4$ represents an organic group; and the one or more pyrazoles formed are of the formula:

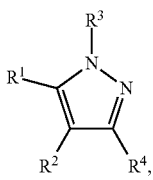

and/or the one or more imidazoles formed are of the formula:

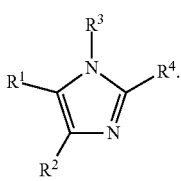

Definitions

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present invention is not intended to describe each embodiment or every implementation of the present invention. Rather, a more complete understanding of the invention will become apparent and appreciated by reference to the following description and claims. Further, it is to be understood that other embodiments may be utilized and structural changes may be made without departing from the scope of the present invention.

DETAILED DESCRIPTION OF ILLUSTRATIVE EMBODIMENTS

Figure 1:
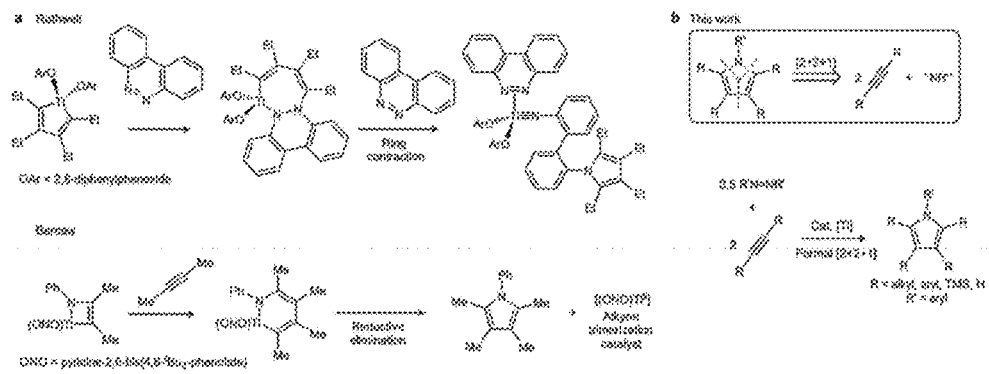
FIG. 1 is a schematic illustration of Ti-mediated oxidative pyrrole formation: a) previous stoichiometric examples of oxidative pyrrole formation from alkynes by Ti complexes; and b) presently disclosed exemplary retrosynthetic disconnection and forward reaction for catalytic formal [2+2+1] oxidative cyclization of alkynes and diazenes.

The stoichiometric oxidative formation of pyrroles from alkynes by Ti complexes has been disclosed. For one example as shown in FIG. 1, Rothwell (i.e., Hill et al., *Inorg. Chem.* 30:1143-1144 (1991)) disclosed that bis(aryloxide) titanacyclopentadienes can insert benzo[c]cinnoline into a Ti—C bond to form a diazatitanacycloheptadiene, which upon heating in the presence of excess benzo[c]cinnoline undergoes ring contraction to generate a Ti imido and a tethered pyrrole. For another example as shown in FIG. 1, Bercaw (i.e., Tonks et al., *Organometallics* 32:3451-3457 (2013)) disclosed the substoichiometric oxidative formation of pyrroles during Ti-catalyzed alkyne hydroamination reactions that were generated via reductive elimination of expanded metallacycles to yield Ti$^{II}$ species.

Disclosed herein is a potential catalytic cycle including reoxidation of Ti$^{II}$ to Ti$^{IV}$=NR with a nitrene oxidant. The reactivity of azobenzene, which may serve as a weakly nucleophilic nitrene source, and simple Ti imidos, (L)$_n$TiCl$_2$(NR) (L=HNMe$_2$, py; n=2, 3; R=Ph, Tol, $^t$Bu) with various alkynes are disclosed herein. For example, the (py)$_3$TiCl$_2$(NR)-catalyzed synthesis of pyrroles through a 3-component formal [2+2+1] oxidative coupling of alkynes and diazenes (FIG. 1, bottom) is disclosed herein. This methodology represents a new retrosynthetic disconnection in the catalytic synthesis of pyrroles, as well as demonstrates a unique example of a catalytic oxidative nitrene transfer by a Ti$^{II}$/Ti$^{IV}$ redox couple.

Accordingly, in one aspect, the present disclosure provides a Ti(IV) compound of the formula:

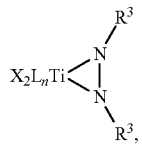

wherein: each R$^3$ independently represents an organic group, each X independently represents an anionic ligand, each L independently represents a neutral ligand, and n=2 to 3.

In another aspect, the present disclosure provides a method of forming a heterocyclic compound including: combining at least one compound having a triple bond, at least one azo compound, and at least one Ti(IV) compound under conditions effective for a [2+2+1] cycloaddition reaction to occur and form one or more heterocyclic compounds.

In some embodiments, the method includes at least one Ti(IV) compound of the formula:

 (i)

L$_n$X$_2$Ti=N—R$^3$ and/or

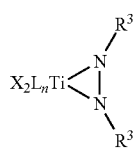 (ii)

wherein: each R$^3$ independently represents an organic group, each X independently represents an anionic ligand, each L independently represents a neutral ligand, and n=2 to 3. In some embodiments, the at least one azo compound is of the formula R$^3$—N=N—R$^3$, wherein each R$^3$ independently represents an organic group.

In some embodiments, the method includes at least one compound having a triple bond that is an alkyne, and the one or more heterocyclic compounds formed include one or more pyrroles.

In certain embodiments, the alkyne is of the formula R$^1$—≡—R$^2$, wherein R$^1$ and R$^2$ each independently represent H or an organic group, or R$^1$ and R$^2$ can be combined to form one or more alicyclic and/or aromatic rings; and the one or more pyrroles formed are of the formulas:

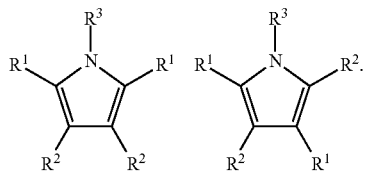

In other certain embodiments, the alkyne is of the formula R$^1$—≡—(CH$_2$)$_y$—≡—R$^2$, wherein R$^1$ and R$^2$ each independently represent H or an organic group, and y=3 to 5; and the one or more pyrroles formed are of the formula:

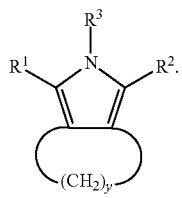

In some embodiments, the method includes at least one compound having a triple bond that is a nitrile-functional compound, and the one or more heterocyclic compounds formed include one or more triazoles.

In certain embodiments, the at least one nitrile-functional compound is of the formula R$^4$—C≡N, wherein R$^4$ represents an organic group; and the one or more triazoles formed are of the formulas:

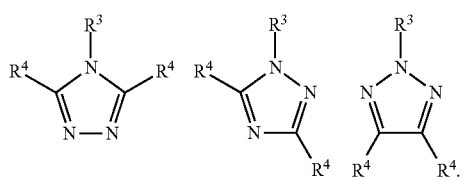

In some embodiments, the method includes at least two compounds having a triple bond including at least one alkyne and at least one nitrile-functional compound, and the one or more heterocyclic compounds formed include one or more pyrazoles and/or imidazoles.

In certain embodiments, the at least one alkyne is of the formula R$^1$—≡—R$^2$, wherein R$^1$ and R$^2$ each independently represent H or an organic group, or R$^1$ and R$^2$ can be combined to form one or more alicyclic and/or aromatic rings; the at least one nitrile-functional compound is of the formula R⁴—C≡N, wherein R⁴ represents an organic group; and the one or more pyrazoles formed are of the formula:

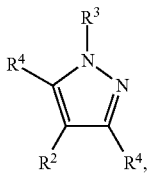

and/or the one or more imidazoles formed are of the formula:

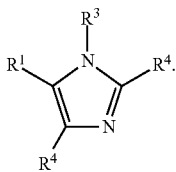

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the reaction of a Ti(IV) compound with an azo compound and a compound having a triple bond to form a heterocyclic compound. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

In certain embodiments of the compositions and methods disclosed herein, each $R^1$, $R^2$, $R^3$, and/or $R^4$ independently represents an alkyl group or an aryl group.

In certain embodiments of the compositions and methods disclosed herein, each $R^1$, $R^2$, $R^3$, and/or $R^4$ independently represents a C1-C20 alkyl group or a C1-C20 aryl group.

In certain embodiments of the compositions and methods disclosed herein, each $R^1$, $R^2$, $R^3$, and/or $R^4$ independently represents a C1-C10 alkyl group or a C1-C10 aryl group.

In certain embodiments of the compositions and methods disclosed herein, each $R^1$, $R^2$, $R^3$, and/or $R^4$ independently represents an alkyl moiety or an aryl moiety.

In certain embodiments of the compositions and methods disclosed herein, each $R^1$, $R^2$, $R^3$, and/or $R^4$ independently represents a C1-C20 alkyl moiety or a C1-C20 aryl moiety.

In certain embodiments of the compositions and methods disclosed herein, each $R^1$, $R^2$, $R^3$, and/or $R^4$ independently represents a C1-C10 alkyl moiety or a C1-C10 aryl moiety.

In some embodiments of the methods disclosed herein, the at least one Ti(IV) compound is present in catalytic amounts. In certain embodiments, the loading of the Ti(IV) compound is greater than or equal to 1% Ti. In other certain embodiments, the loading of the Ti(IV) compound is greater than or equal to 2.5% Ti.

In some embodiments of the methods disclosed herein, conditions effective for a [2+2+1] cycloaddition reaction to occur include the presence of a solvent (e.g., a non-coordinating solvent). Exemplary solvents include, but are not limited to, toluene, fluorobenzene, p-chlorotoluene, α,α,α-trifluorotoluene (TFT), benzene, an alkane, a haloalkane, and combinations thereof. Exemplary haloalkanes include, but are not limited to, dichloromethane (DCM), dichloroethane, tetrachloroethane, and combinations thereof.

In some embodiments of the methods disclosed herein, conditions effective for a [2+2+1] cycloaddition reaction to occur include essentially anhydrous conditions.

In some embodiments of the methods disclosed herein, conditions effective for a [2+2+1] cycloaddition reaction to occur include essentially the absence of oxygen.

In some embodiments of the compositions and methods disclosed herein, each X independently represents an inorganic anionic ligand.

In some embodiments of the compositions and methods disclosed herein, each X is independently selected from the group consisting of halides, aryloxides, amides, alkoxides, cyclopentadienyl ligands, non-coordinating counterions, and combinations thereof.

In some embodiments of the compositions and methods disclosed herein, each L independently represents a neutral organic coordinating ligand.

In some embodiments of the compositions and methods disclosed herein, each L is selected from the group consisting of pyridine, disubstituted amines, trisubstituted amines, phosphines, bis-phosphines, lutidine, 2-methylpryidine, 4-dimethylaminopyridine (DMAP), and combinations thereof.

Results and Discussion

Figure 2:
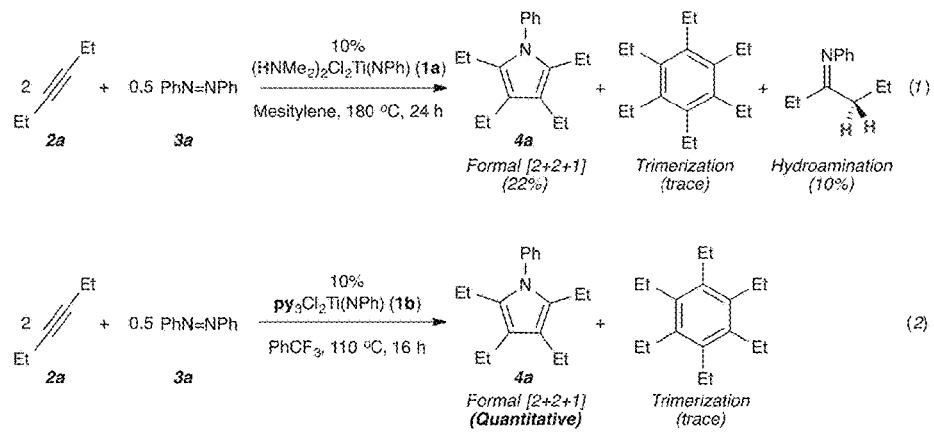
FIG. 2 is a schematic illustration of exemplary catalytic experiments showing that aprotic Ti imido complexes can be highly efficient catalysts for [2+2+1] cyclization.

Reaction of 10 mol % 1a with 2 equivalents of 3-hexyne (2a) and 0.5 equivalents of azobenzene (3a) in mesitylene at 180° C. for 24 hours yielded catalytic production of N-phenyl-2,3,4,5-tetraethylpyrrole (4a) (22%), the formal [2+2+1] oxidative coupling product of 2 alkynes and 0.5 azobenzenes (FIG. 2, eq 1). Additionally, stoichiometric amounts (10%) of the hydroamination product, N-phenylhexan-3-imine, and small amounts of the cyclotrimerization product, hexaethylbenzene, were observed. While the yield and selectivity of this initial reaction are poor, three observations can be made: first, azobenzene is capable of turning over the catalytic reaction through reoxidation of low valent Ti intermediates; second, the [2+2+1] reaction is competing with hydroamination and the two reaction cycles likely share a common Ti intermediate; and third, that $Ti^{II}$ intermediates must be involved due to the presence of competitive alkyne trimerization (Ozerov et al., *J. Am. Chem. Soc.* 122:6423-6431 (2000)). In this case, hydroamination occurs via double protonation of an azatitanacyclobutene intermediate by the 2 equivalents of dimethylamine present in the Ti imido precatalyst.

By utilizing an aprotic catalyst, $(py)_3TiCl_2(NPh)$ (1b) (Blake et al., *J. Chem. Soc. Dalton Trans.* 1549-1558 (1997)), quantitative conversion to the desired [2+2+1] product was observed with minimal competing cyclotrimerization and no hydroamination (FIG. 2, eq 2). Interestingly, both NPh units in azobenzene are incorporated into the product. When using 10 mol % of $(py)_3TiCl_2(Ntol)$ (1c) or $(py_3)TiCl_2(N^tBu)$ (1d), 10% of the product contains tolyl- or $^tBu$-functionalized pyrrole, indicating that reactivity occurs through the imido functionality and that virtually all of the Ti catalyst undergoes reaction.

Figure 3:
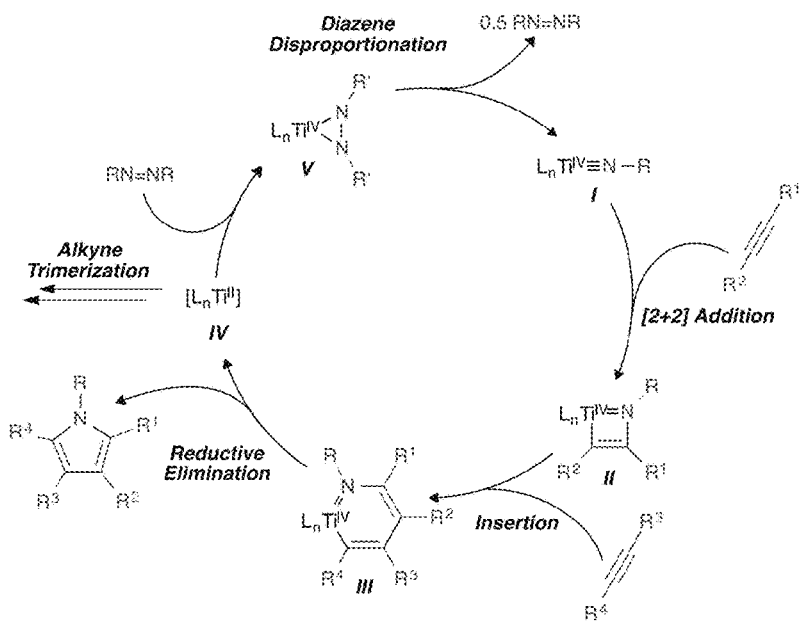
FIG. 3 is a schematic illustration of a possible mechanism for Ti-catalyzed formal [2+2+1] oxidative cyclization of exemplary alkynes and diazenes proceeding through a $Ti^{II}/Ti^{IV}$ redox couple.

The preliminary mechanism for the catalytic oxidative formal [2+2+1] cyclization of alkynes and diazenes is presented in FIG. 3. First, a $Ti^{IV}$ imido (I) undergoes [2+2] addition with an alkyne to form an azatitanacyclobutene (II), identical to the first step for Ti-catalyzed hydroamination. (Müller et al., *Chem. Rev.* 108:3795-3892 (2008); Vujkovic et al., *Organometallics* 27:2518-2528 (2008); Straub et al., *Angew. Chem. Int. Ed. Engl.*, 40:4632-4635 (2001); and Weitershaus et al., *Dalton Trans.* 4586-4602 (2009)). This step is supported by the initial catalytic experiments with 1a, where hydroamination competed with [2+2+1] cyclization. Next, a second equivalent of alkyne inserts into the azatitanacyclobutene to form an azatitanacyclohexadiene (III). Second insertions into azatitanacycles are quite rare, but have previously been observed by Mountford (e.g., alkynes, stoichiometric, in Vujkvic et al., *Organometallics* 26:5522-5534 (2007)) and Odom (isocyanides, catalytic in Barnea et al., *Organometallics* 28:3876-3881 (2009))

After second insertion, reductive elimination from III yields the pyrrole product and a $Ti^{II}$ intermediate (IV). The resulting $Ti^{II}$ intermediate can then either unproductively trimerize alkyne, (Ozerov et al., *J. Am. Chem. Soc.* 122: 6423-6431 (2000)) or be trapped by azobenzene to form a $Ti^{II}$ $\eta^2$-azobenzene adduct (V) (e.g., Tripepi et al., *J. Organomet. Chem.* 593-594:354-360 (2000); Kaleta et al., *Inorganica Chim. Acta* 370:187-190 (2011); Kaleta et al., *Organometallics* 29:2604-2609 (2010); and Retbøll et al., *Inorg. Chem.* 33:6403-6405 (1994)) which then disproportionates into a $Ti^{IV}$ imido (I) (e.g., Duchateau et al., *Inorg. Chem.* 30:4863-4866 (1991); Gray et al., *Inorg. Chem.* 37:1-4 (1998); and Hill et al., *Angew. Chem. Int. Ed. Engl.* 102: 664-665 (1990)) to close the catalytic cycle. This reductive elimination may be facilitated by the coordination of azobenzene or alkyne, either of which could act as a "redox-noninnocent" ligand and immediately accept the electrons from reductive elimination to avoid a longlived $Ti^{II}$ intermediate. Under either scenario, the binding competition of azobenzene and alkyne determines whether alkyne trimerization or productive reoxidation occurs.

Figure 4:
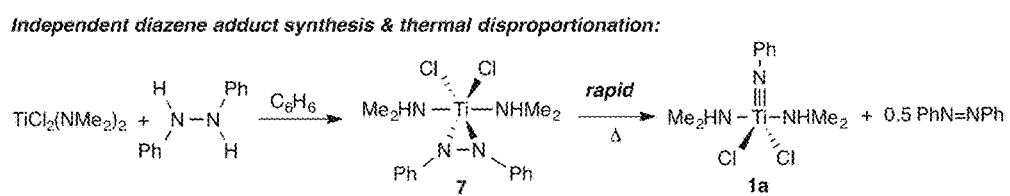
FIG. 4 is a schematic illustration of exemplary synthesis and potential mechanisms for an exemplary disproportionation of 7 to 1a. For some embodiments, experimental evidence indicates that the dimerization pathway may be more likely.
Figure 4:
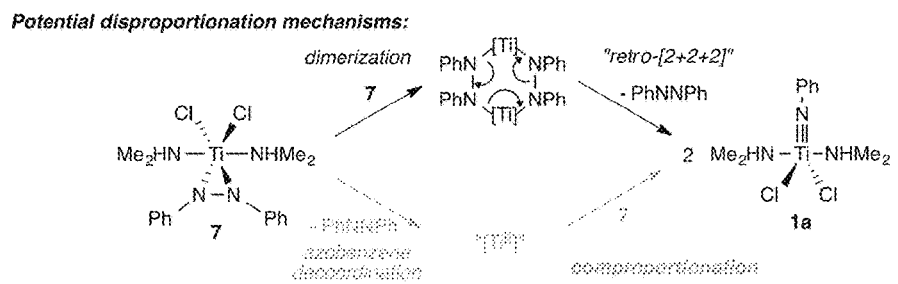

The reoxidation of the transient $Ti^{II}$ species to a $Ti^{IV}$ imido may involve a disproportionation of an $\eta^2$-azobenzene complex into a $Ti^{IV}$ imido and 0.5 equivalents of azobenzene. To examine the stoichiometric viability of this rather unique catalytic reoxidation mechanism a Ti $\eta^2$-azobenzene complex, $(HNMe_2)_2TiCl_2(PhNNPh)$ (7), which is similar in structure to the proposed $Ti^{II}$ $\eta^2$-azobenzene adduct V, was synthesized via protonolysis of $TiCl_2(NMe_2)_2$ by 1,2-diphenylhydrazine (FIG. 4). The X-ray structure of 7 reveals an N—N bond length of 1.420(3) Å, indicating a reduced $\eta^2$-PhN-NPh$(^{2-})$ hydrazido unit bound to a $Ti^{IV}$ center instead of a $Ti^{II}$ azobenzene adduct (e.g., Hill et al., *Angew. Chem. Int. Ed. Engl.* 102:664-665 (1990); and Retbøll et al., *Inorg. Chem.* 33:6403-6405 (1994)). Thermolysis of 7 in α,α,α-trifluorotoluene (TFT) results in rapid, full conversion to the $Ti^{IV}$ imido 1a by $^1H$ NMR with concomitant production of 0.5 equivalents of azobenzene, consistent with the $\eta^2$-azobenzene adduct being a viable catalytic intermediate.

Complex 7 could disproportionate to 1a through two limiting pathways: first, by dimerization (Goetze et al., *Eur. J. Inorg. Chem.* 1849-1854 (2000)) to generate a $Ti_2N_4$ species that could then retrocyclize into 1a and free azobenzene (FIG. 4, top pathway); or alternately, by decoordination of azobenzene to make a free $Ti^{II}$ species that could then comproportionate (Gray et al., *Inorg. Chem.* 37:1-4 (1998)) with another equivalent of 7 to generate two equivalents of 1a (FIG. 4, bottom pathway). The disproportionation likely occurs through the dimerization pathway because addition of tolNNtol to 7 yields neither tolyl-functionalized Ti imdo nor tolNNPh crossover products upon heating and disproportionation.

Notably, later transition metals and complexes with redox active ligands have been reported to perform the reverse reaction—coupling metal imidos to generate diazenes (e.g., Munhá et al., *Dalton Trans.* 42:3751-3766 (2013); Zarkesh et al., *Angew. Chem. Int Ed.* 47:4715-4718 (2008); Mankad et al., *J. Am. Chem. Soc.* 132:4083-4085 (2010); and Mansuy et al., *J. Am. Chem. Soc.* 104:4487-4489 (1982)). For this [2+2+1] coupling, the large thermodynamic preference for $Ti^{II}$ oxidation drives the reaction to favor diazene cleavage to form imidos. The use of diazenes to promote Ti reoxidation can enable catalysis; other "nitrene" oxidants such as aryl azides or PhINTs do not yield productive reactivity.

The scope of the reaction was examined using a number of alkynes at 110° C. in TFT. The results of reactions with internal and terminal alkynes, diynes, and enynes are shown in Table 1. Overall, internal and terminal alkynes with alkyl, aryl and silyl groups are well-tolerated; however, alkynyl esters, tethered alkyl ethers, and bis(trimethylsilyl)acetylene do not react under typical reaction conditions.

TABLE 1

Initial alkyne scope of Ti-catalyzed formal oxidative [2 + 2 + 1] cyclization.[a]

$$3 \, R^1\text{—}\equiv\text{—}R^2 + 0.5 \, PhN{=}NPh \xrightarrow[\text{PhCF}_3, \; 110°C, \; 16\,h]{10\% \; py_3Cl_2Ti(Nh) \; (1b)} \text{4a-4n} + \text{5d-5j} + \text{6d-6j (when } R^1 \neq R^2\text{)}$$

| Alkyne | Product(s) (ratio) | % Yield (NMR)[b] |
|---|---|---|
| 2a[c] ($R^1=R^2=$Et) | 4a | 85 (96) |
| 2b ($R^1=R^2=$Me) | 4b | 76 (98) |
| 2c ($R^1=R^2=$Ph) | 4c | 26 (51) |
| 2d ($R^1=$Me; $R^2={}^i$Pr) | 4d (0.72); 5d (1.0); 6d (0.35) | 30 (71) |
| 2e ($R^1={}^n$Pr; $R^2=$TMS) | 4e (0.0); 5e (1.0); 6e (0.0) | (78) |
| 2f ($R^1=$Me; $R^2=$Ph) | 4f (0.45); 5f (1.0); 6f (0.77) | 60 (91) |
| 2g[d] ($R^1=$H; $R^2=$Ph) | 4g (0.0); 5g (1.0); 6g (0.25) | (32) |
| 2h ($R^1=$H; $R^2={}^n$Bu) | 4h (0.13); 5h (1.0); 6h (0.13) | 36 (57) |
| 2l ($R^1=$H; $R^2={}^t$Bu) | 4i (0.0); 5i (1.0); 6i (0.0) | 55 (92) |
| 2j[d] ($R^1=$H; $R^2=$TMS) | 4j (min)[e]; 5j (max)[e]; 6j (min)[e] | (52) |
| 2k ($R^1=$Me; $R^2=(CH_2)_3$—C≡C—Me) | 4k (1,3-dimethyl-2-phenyl-2,4,5,6-tetrahydrocyclopenta[c]pyrrole) | (76) |
| 2l ($R^1=$Ph; $R^2=(CH_2)_3$—C≡C—Ph) | 4l (1,2,3-triphenyl-2,4,5,6-tetrahydrocyclopenta[c]pyrrole) | 46 |
| 2m ($R^1=$Et; $R^2=(CH_2)_4$—C≡C—Et) | 4m (1,3-diethyl-2-phenyl-4,5,6,7-tetrahydro-2H-isoindole) | 65 (95) |
| 2n ($R^1=$nBu; $R^2=(CH_2)_3$—CH=CH$_2$) | 4n (1-(2-methylcyclopent-1-en-1-yl)pentan-1-one) | 50[f] (83) |
| 2o ($R^1=$H; $R^2=CH_2$—O—CH$_2$—C≡C—H) | No reaction | |
| 2p ($R^1=$Me; $R^2=CH_2$—O—CH$_2$—CH=CH$_2$) | No reaction | |
| 2q ($R^1=R^2=$TMS) | No reaction | |
| 2r ($R^1=R^2=$CO$_2$Me) | No reaction | |

[a]Conditions: 1.21 mmol 2 (6 equiv), 0.20 mmol 3 (1 equiv), 0.020 mmol 1b (0.1 equiv), 1 mL CF$_3$Ph, 16 hours.
[b]NMR yield based on 3a with Ph$_3$CH internal standard.
[c]Apparent turnover frequency based on initial rates is approximately 1 hour$^{-1}$.
[d]6 equivalents of 3a; yield based on 2.
[e]Overlapping $^1$H NMR signals prevent accurate integration: >80% 5j.
[f]Isolated yield upon hydrolysis to the corresponding ketone.

Alkynes that are known to rapidly undergo metal-catalyzed cyclotrimerization utilize excess azobenzene to give high yields. For example, phenylacetylene (2g) gave almost no pyrrole products (<5%) under typical reaction conditions; instead, the major products observed were 1,2,4-triphenylbenzene and 1,3,5-triphenylbenzene. Increased yield of the pyrrole regioisomers 5g and 6g can be obtained by using a 6-fold excess of 3a to favor azobenzene binding over phenylacetylene binding to the Ti$^{II}$ intermediate IV.

Further evidence for the binding competition of alkyne and azobenzene can be observed in the reactions of tethered diynes. Reaction of 2,7-nonadiyne (2k) with stoichiometric azobenzene resulted in 22% 4k with the remainder of 2k converted to the tethered diaryl trimer that results from three diynes cyclotrimerizing; increasing the concentration of azobenzene significantly improved the yield of 4k. Conversely, reaction of 3,9-dodecadiyne (2m) with only one equivalent of azobenzene gave high yield for the fused pyrrole 4m, highlighting that subtle changes in ring size can shift the competition to favor product formation even at low azobenzene concentrations.

Because the mechanism of first and second alkyne insertions are different ([2+2] addition versus migratory insertion), there is great potential to expand catalysis to include the selective coupling of two different unsaturated substrates: for example, compared to alkynes, alkenes do not facilely undergo [2+2] reaction with Ti imidos (e.g., Müller et al., Chem. Rev. 108:3795-3892 (2008); and Straub et al., Angew. Chem. Int. Ed. Engl., 40:4632-4635 (2001)), but will rapidly undergo migratory insertion. Thus it may be possible to catalytically couple alkynes and alkenes with Ti imidos. Accordingly, tethered enyne 2n undergoes alkyne [2+2] addition followed by alkene insertion to generate an azatitanacyclohexene. However, instead of reductive C—N bond formation to yield a dihydropyrrole, the metallacycle rearranges prior to reductive elimination to yield the α,β-unsaturated imine 4n.

Figure 5:
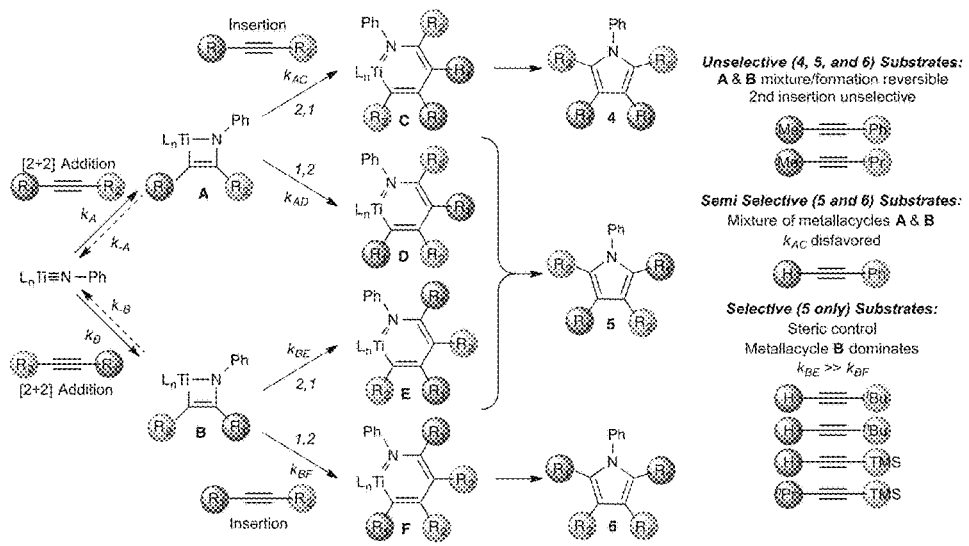
FIG. 5 is a schematic illustration of a mechanistic scheme illustrating selectivity differences between various exemplary unsymmetric alkynes.

Coupling of untethered unsymmetrical alkynes can potentially yield mixtures of regioisomers. Regioselectivity may be determined during two steps of catalysis (FIG. 5): first, by the orientation of the alkyne during [2+2] addition to give one of two regioisomeric azametallacyclobutenes (A and B); and second, during alkyne insertion, which can proceed via 1,2- or 2,1-insertion into either A or B, ultimately yielding one of four regioisomeric azametallacyclohexadienes (C, D, E, or F) that then undergo reductive elimination to give the three possible pyrrole regioisomers 4, 5, and 6. Regiocontrol is highly substrate dependent (Table 1): 2d and 2f are essentially nonselective for all 3 possible regioisomers; phenylacetylene (2g) is moderately selective for the 2,4-disubstituted regioisomer 5g (4g:5g:6g=0:4.0:1.0); while the terminal and TMS-protected alkynes 2e, 2h, 2i, and 2j are highly selective for regioisomer 5.

The origin of selectivity in the [2+2+1] couplings of unsymmetric alkynes can be qualitatively determined by comparing the [2+2+1] regioselectivity to the selectivity of alkyne hydroamination catalyzed by 1b, since both reactions share common [2+2] regioisomeric metallacycle intermediates (A and B) (e.g., Gräbe et al., *Eur. J. Org. Chem.* 28:4815-4823 (2008)). Hydroamination of $^t$BuCCH (2i) is completely selective for the sterically-preferred antimarkovnikov imine product resulting from protonolysis of metallacycle B. During [2+2+1] catalysis with 2i, only 5i, which could arise from either metallacycles D or E, is observed. Based on the selectivity for B observed in the initial [2+2] step, it may be likely that 5i results only from sterically-preferred 2,1-insertion of alkyne into B to yield metallacycle D. In the cases where 5 is the predominant regioisomeric product, selectivity for both [2+2] and $2^{nd}$ insertion may be controlled by alkyne sterics.

Conversely, hydroamination of phenylacetylene (2g) is less selective, yielding a 1:2 mixture of the imine products resulting from protonolysis of A and B, respectively. During [2+2+1] catalysis with 2g, products arising from metallacycles D, E, and F are observed. In this case, it may be likely that the initial [2+2] step is similarly unselective as in hydroamination, and the observed product distribution is a result of moderately selective insertion of 2g into A and B, wherein the 2,1-addition leading to metallacycle C is disfavored over the other insertion pathways.

Interestingly, 2d yields an unselective mixture of all 3 possible pyrrole regioisomers, yet hydroamination is completely selective for the methyl benzyl imine product that results from protonolysis of only one of the metallacycles. In this case, the [2+2] reaction may be reversible on the timescale of second alkyne insertion, allowing for unselective secondary insertion of the sterically and electronically poorly-differentiated sides of the alkyne, yielding a mixture of all products.

Figure 8:
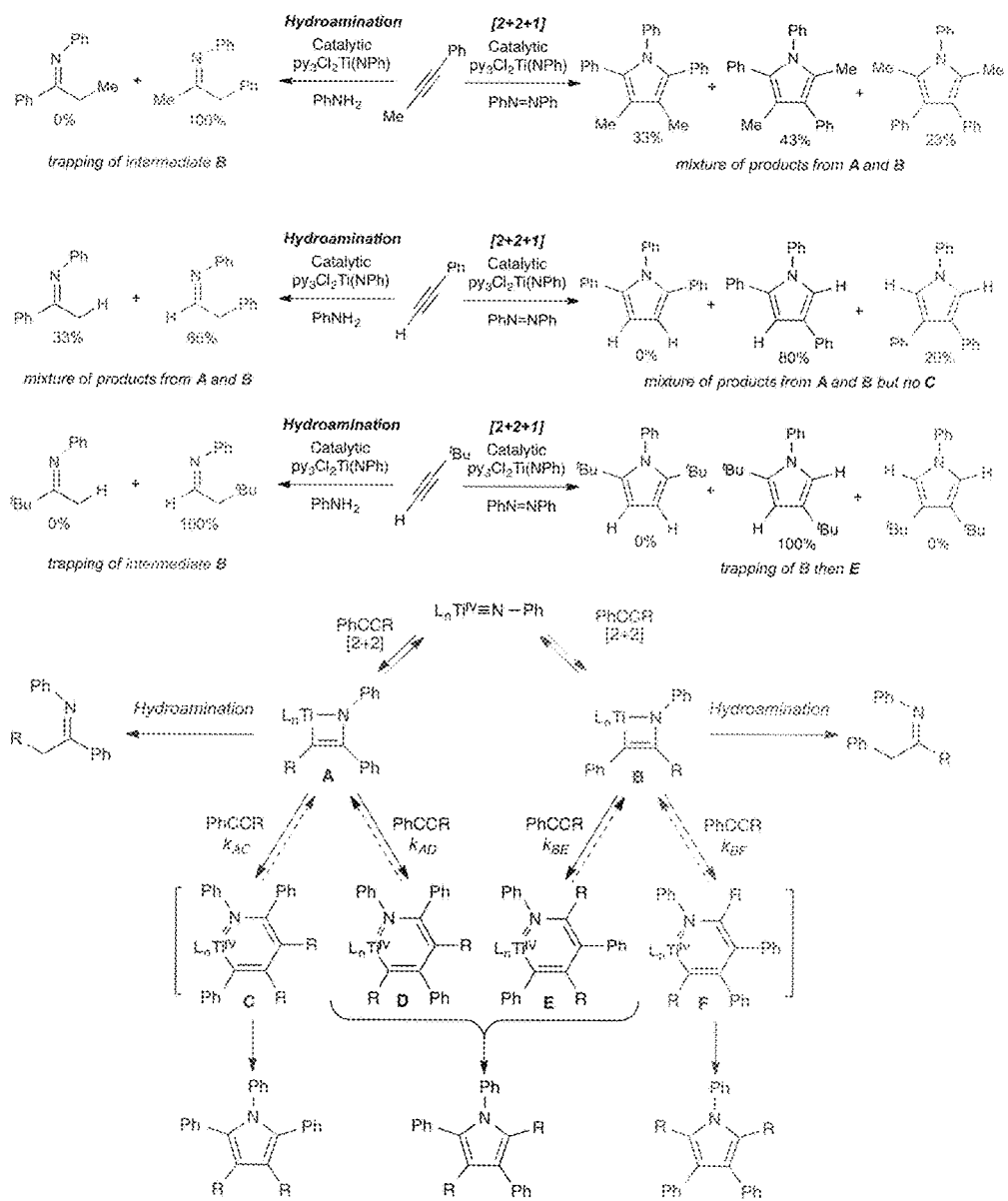
FIG. 8 is a schematic diagram illustrating the origin of each possible regioisomer of hydroamination and [2+2+1] cyclization catalyzed by $py_3Cl_2Ti(NPh)$.
Figure 9:
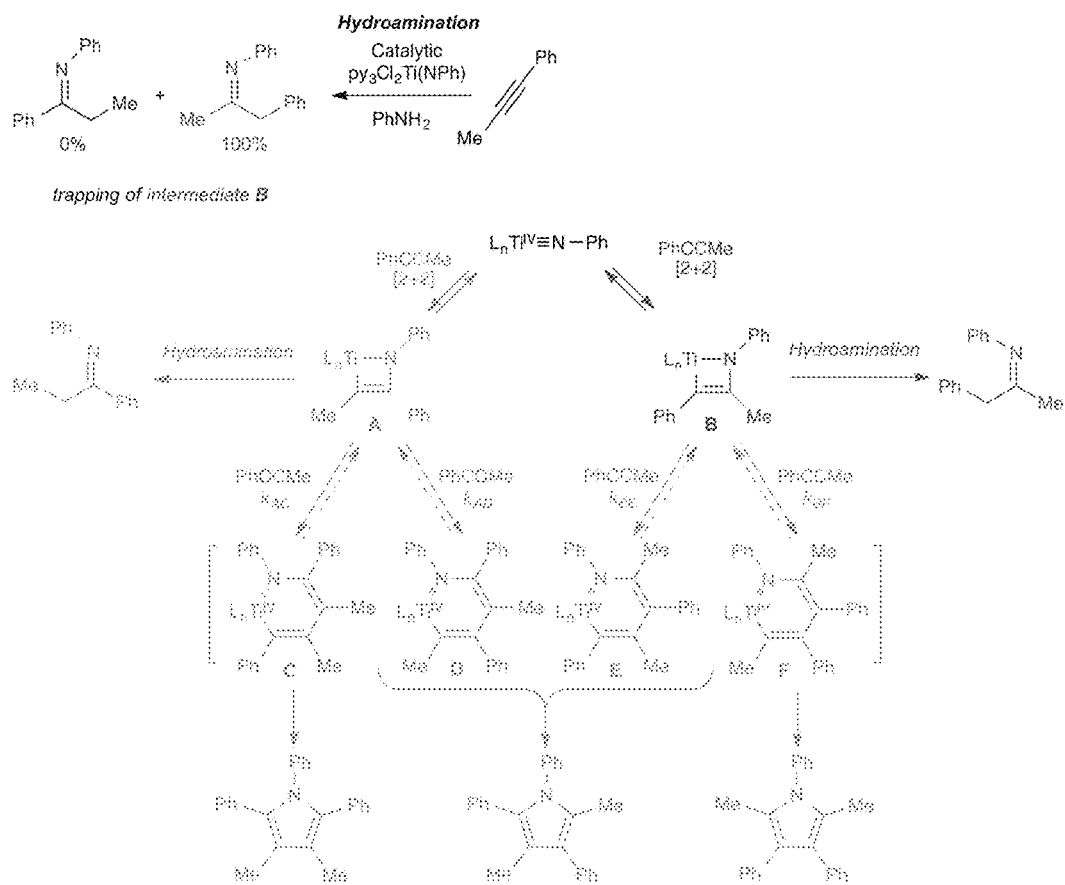
FIG. 9 is a schematic diagram illustrating operative pathways in the hydroamination of PhCCMe catalyzed by $py_3Cl_2Ti(NPh)$. Greyed-out portions were not observed to occur.
Figure 10:
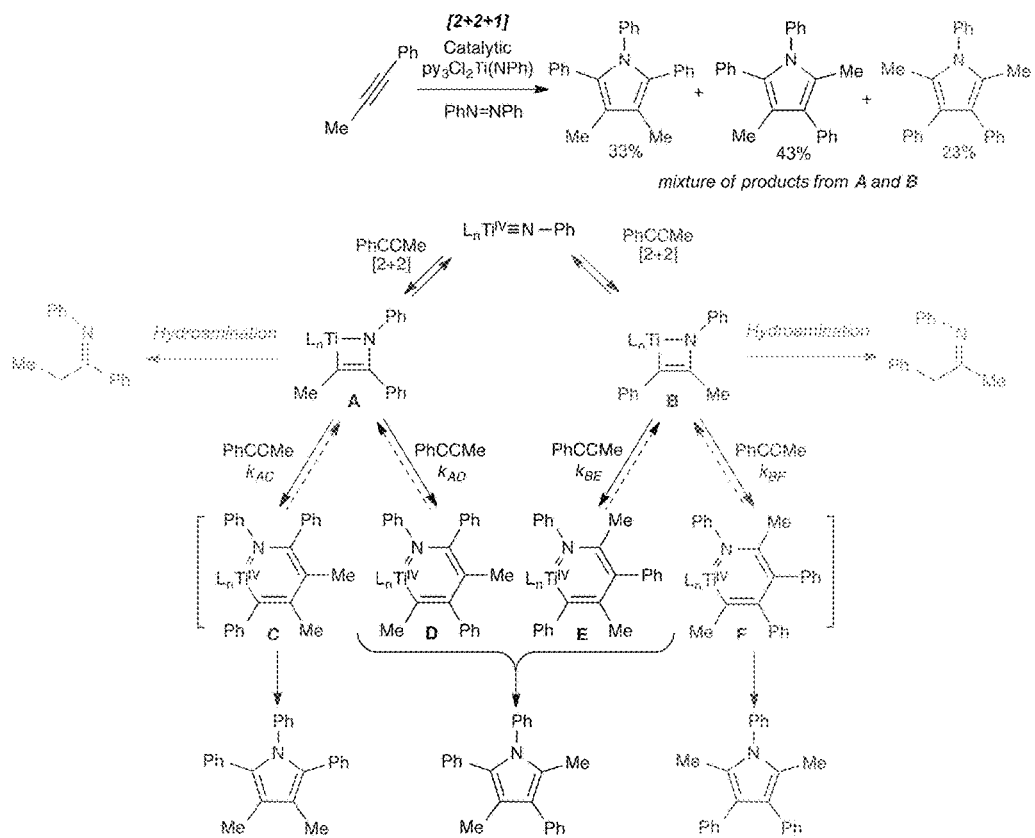
FIG. 10 is a schematic diagram illustrating operative pathways in the [2+2+1] cyclization of PhCCMe catalyzed by $py_3Cl_2Ti(NPh)$. Greyed-out portions were not observed to occur.
Figure 11:
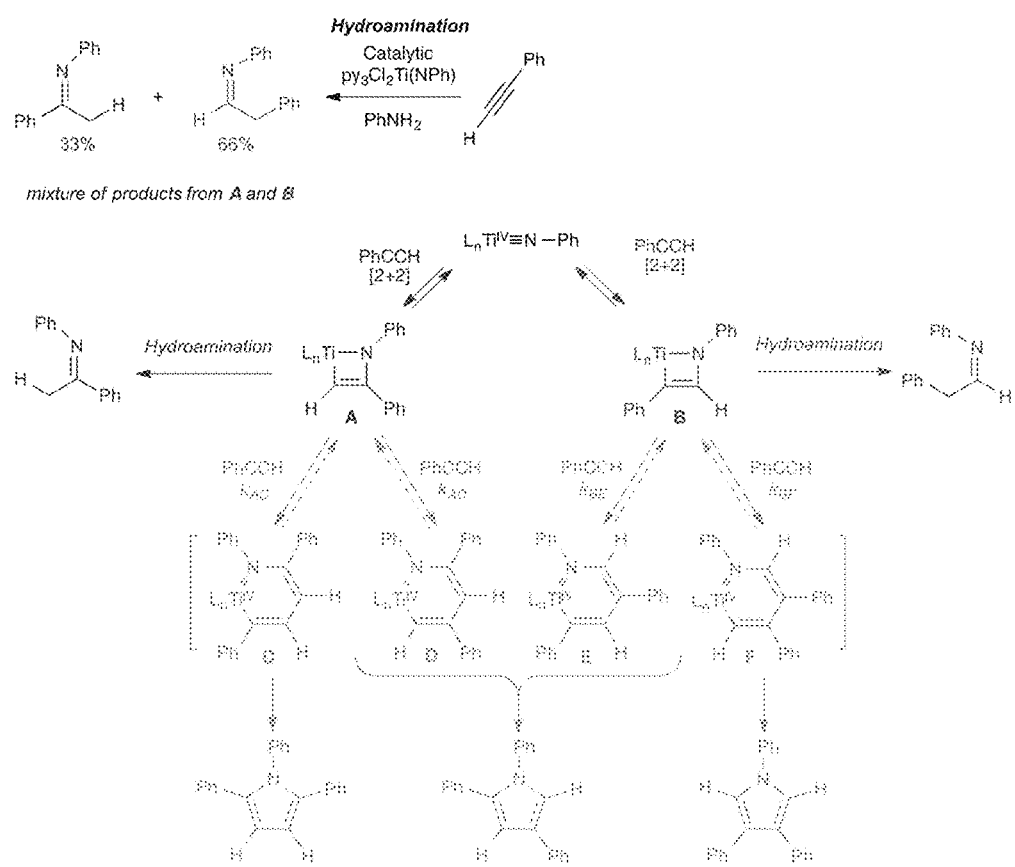
FIG. 11 is a schematic diagram illustrating operative pathways in the hydroamination of PhCCH catalyzed by $py_3Cl_2Ti(NPh)$. Greyed-out portions were not observed to occur.
Figure 12:
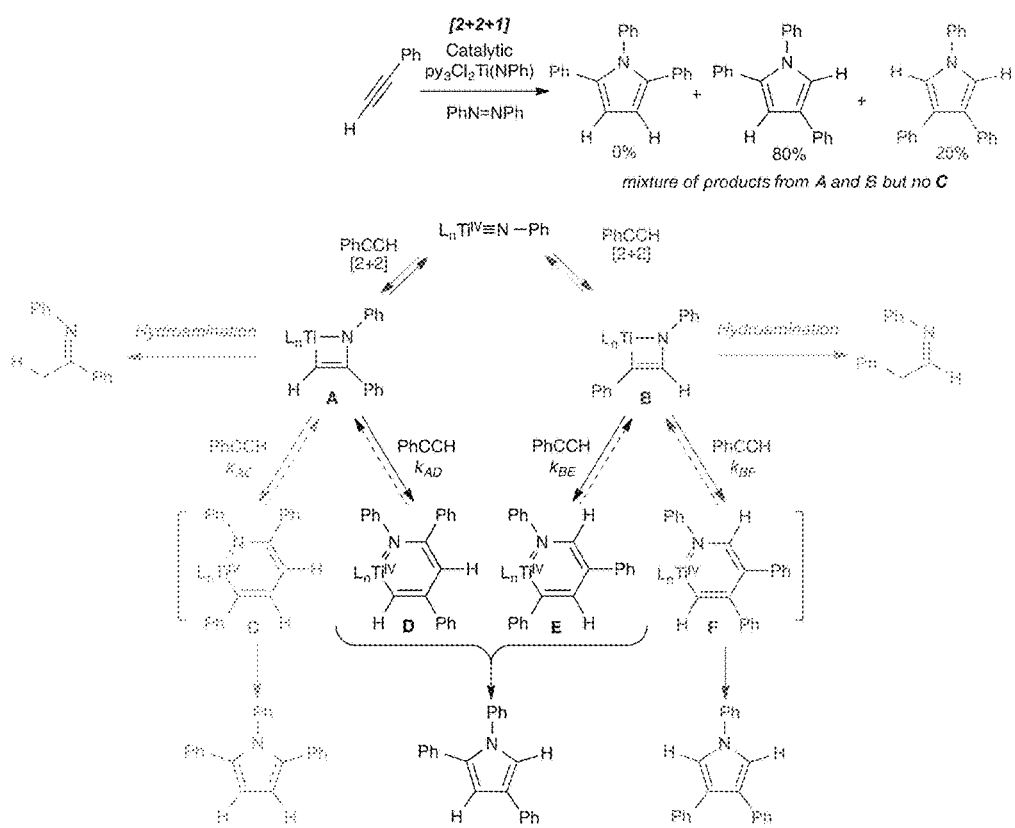
FIG. 12 is a schematic diagram illustrating operative pathways in the [2+2+1] cyclization of PhCCH catalyzed by $py_3Cl_2Ti(NPh)$. Greyed-out portions were not observed to occur.
Figure 13:
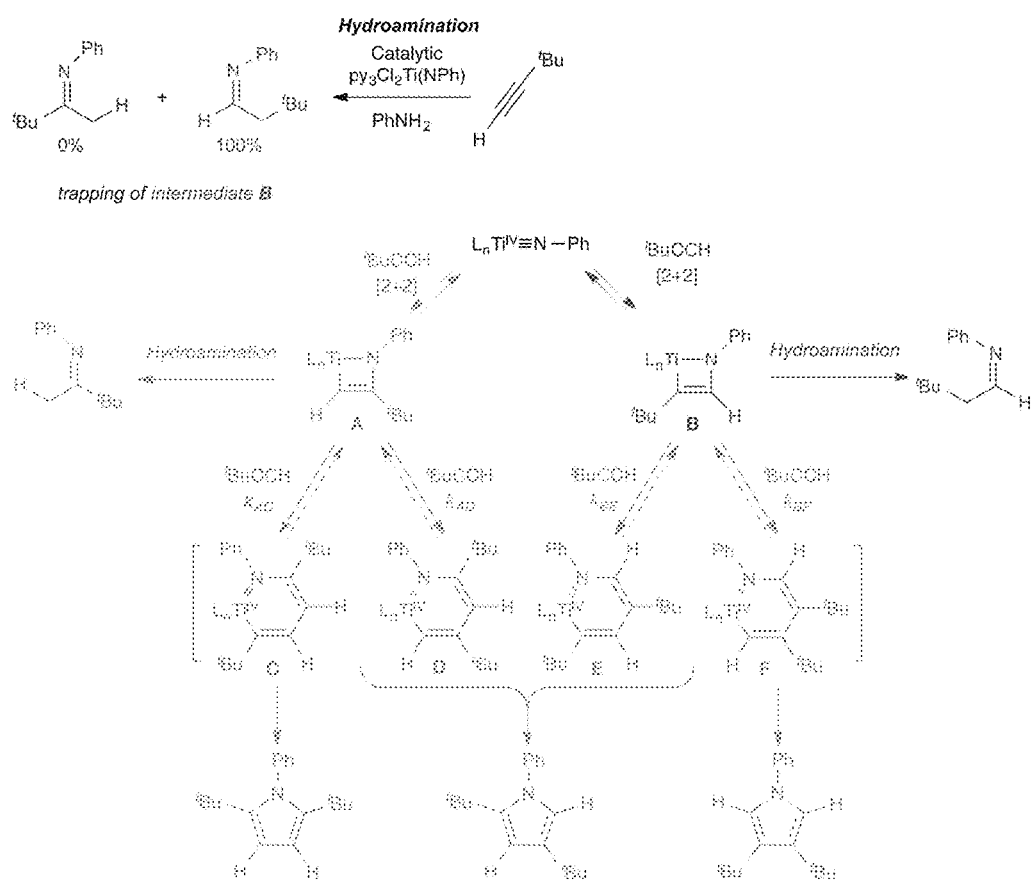
FIG. 13 is a schematic diagram illustrating operative pathways in the hydroamination of tBuCCH catalyzed by $py_3Cl_2Ti(NPh)$. Greyed-out portions were not observed to occur.
Figure 14:
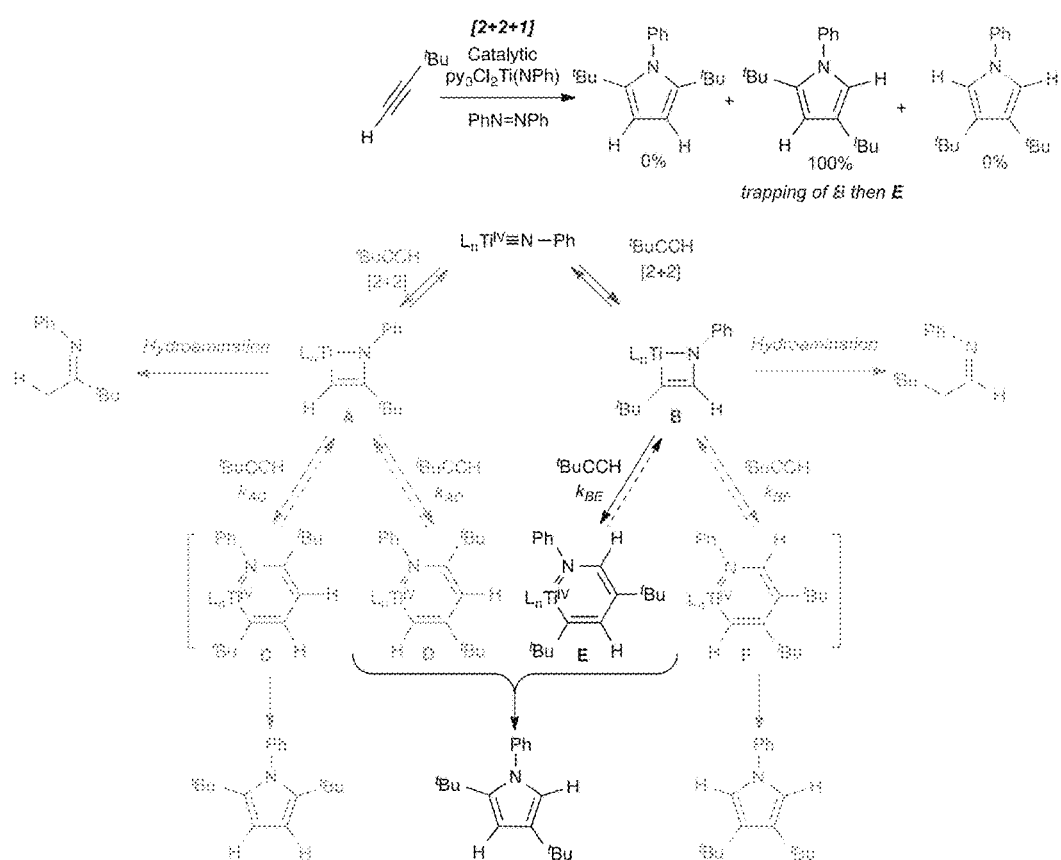
FIG. 14 is a schematic diagram illustrating operative pathways in the [2+2+1] cyclization of tBuCCH catalyzed by py$_3$Cl$_2$Ti(NPh). Greyed-out portions were not observed to occur.

A summary illustrating observed regioselectivity is graphically illustrated in FIGS. 8-14. FIG. 8 is a schematic diagram illustrating the origin of each possible regioisomer of hydroamination and [2+2+1] cyclization catalyzed by py$_3$Cl$_2$Ti(NPh). FIG. 9 is a schematic diagram illustrating operative pathways in the hydroamination of PhCCMe catalyzed by py$_3$Cl$_2$Ti(NPh). FIG. 10 is a schematic diagram illustrating operative pathways in the [2+2+1] cyclization of PhCCMe catalyzed by py$_3$Cl$_2$Ti(NPh). FIG. 11 is a schematic diagram illustrating operative pathways in the hydroamination of PhCCH catalyzed by py$_3$Cl$_2$Ti(NPh). FIG. 12 is a schematic diagram illustrating operative pathways in the [2+2+1] cyclization of PhCCH catalyzed by py$_3$Cl$_2$Ti(NPh). FIG. 13 is a schematic diagram illustrating operative pathways in the hydroamination of tBuCCH catalyzed by py$_3$Cl$_2$Ti(NPh). FIG. 14 is a schematic diagram illustrating operative pathways in the [2+2+1] cyclization of tBuCCH catalyzed by py$_3$Cl$_2$Ti(NPh). Greyed-out portions were not observed to occur.

Further substrate scope analysis was performed using substituted aryl diazenes (Table 2). Tolyl substituted diazenes 3b and 3c reacted similarly to the parent azobenzene; however, more sterically encumbered diazene 3d was lower yielding. Electron-rich diazene 3e that contains a heteroatom-functionalized arene also gives excellent conversion to 4ae. Of synthetic importance, the N-methoxyphenyl substituent in 4ae can potentially be oxidatively deprotected to yield the N-unsubstituted pyrrole. Finally, utilizing an asymmetric diazene (3i) yields both products 4a and 4ai in a 1:1 ratio, indicating both halves of the diazene are incorporated into the pyrroles at roughly equal rate.

TABLE 2

Initial diazene scope of Ti-catalyzed formal oxidative [2 + 2 + 1] cyclization.[a]

| Diazene | Product | % Yield (NMR)[b] |
|---|---|---|
| 3b (R=R'=4-MePh) | 4ab (R=4-MePh) | 85 (86) |
| 3c (R=R'=2-MePh) | 4ac (R=2-MePh) | 71 (83) |
| 3d (R=R'=3,5-di-$^t$BuPh) | 4ad (R=3,5-di-$^t$BuPh) | (32) |
| 3e (R=R'=4-MeoPh) | 4ae (R=4-MeoPh) | 66 (86) |
| 3f (R=R'=4-CF$_3$Ph) | no reaction | |
| 3g (R=R'=benzyl) | 4ac (R=benzyl) | Trace[c] |
| 3h (R=R'=C(O)O$^i$Pr) | no reaction | |
| 3i (R=Ph; R'=p-NMe$_2$Ph) | 4a:4ai (1:1) | (69) |

[a]Conditions: 1.21 mmol 2 (6 equiv), 0.20 mmol 3 (1 equiv), 0.020 mmol 1b (0.1 equiv), 1 mL CF$_3$Ph, 16 hours. Reactions performed at 140° C.
[b]NMR yield based on 3a with Ph$_3$CH internal standard.
[c]Benzyl-N=N-benzyl undergoes radical decomposition under the reaction conditions.

Figure 6:
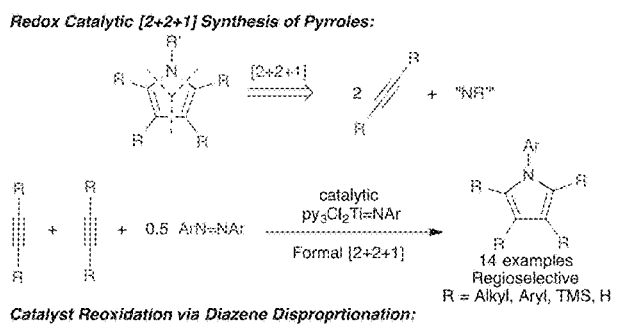
FIG. 6 is a schematic illustration of and exemplary redox catalytic [2+2+1] synthesis of pyrrole; and catalyst reoxidation via an exemplary diazene disproportionation.

In summary, a simple Ti imido precatalyst, py$_3$Cl$_2$Ti(NPh), is capable of performing inter- and intramolecular oxidative coupling of alkynes or enynes with diazenes to generate polysubstituted pyrroles (FIG. 6). This reaction is a unique example of catalytic oxidative C—N bond formation with a Group 4 early transition metal and of catalytic formal [2+2+1] 6-electron cyclization with a nitrene feedstock. A key feature of the catalytic cycle is the cleavage of the N=N double bond of an aryl diazene, which may occur through the disproportionation of a $Ti^{II} \eta^2$-diazene adduct to reform a $Ti^{IV}$ imido. Initial studies have revealed the regioselectivity of the alkyne coupling may be under substrate control. However, given recent successes in ligand development for selective and functional group tolerant early transition metal-catalyzed Pauson-khand (Hicks et al., *J. Am. Chem. Soc.* 118:11688-11689 (1996)) and hydroamination (Müller et al., *Chem. Rev.* 108:3795-3892 (2008); and Yim et al., *J. Org. Chem.* 79:2015-2028 (2014)) reactions, it may be possible to apply similar principles to advance substrate scope and selectivity in the catalytic formal [2+2+1] reaction.

The present invention is illustrated by the following examples. It is to be understood that the particular examples, materials, amounts, and procedures are to be interpreted broadly in accordance with the scope and spirit of the invention as set forth herein.

EXAMPLES

General Considerations

All air- and moisture-sensitive compounds were manipulated in a glovebox under a nitrogen atmosphere. Solvents for air- and moisture-sensitive reactions were vacuum transferred from sodium benzophenone ketyl for tetrahydrofuran (THF), diethyl ether ($Et_2O$), pentane, $d_6$-benzene, and $d_8$-toluene; or $CaH_2$ for dichloromethane (DCM) and trifluorotoluene (TFT); or predried on a Vacuum Atmospheres Solvent Purification System and filtered through activated basic alumina for hexanes, toluene, and benzene. 2a-2j, 2m, 3a, 3h and 3i were purchased from Sigma, Aldrich, TCI America, and Alfa Aesar. $Ti(NMe_2)_4$ (Benzing et al., *Chem. Ber.* 94:2263-2267 (1961)), $TiCl_2(NMe_2)_2$ (Bradley et al., *J. Chem. Soc.* 3857-3861 (1960)), $(py)_3TiCl_2(NAr)$ (Blake et al., *J. Chem. Soc. Dalton Trans.* 1539-1558 (1997)), $(HNMe_2)_2TiCl_2(NAr)$ (Adams et al., *Inorg. Chem.* 44:2882-2894 (2005)), $(ONO)Ti(NAr)(HNMe_2)$ (Tonks et al., *Organometallics* 32:3451-3457 (2013)), 3b-d,f (Yu et al., *Tetrahedron* 62:10303-10310 (2006)), 3e (Nesterowicz et al., *Polish J. of Chem.* 55:1085-1092 (1981)), 3g (Bandlish et al., *J. Am. Chem. Soc.* 20:5856-5862 (1975)), and 2k (Amatore et al., *J. Am. Chem. Soc.* 135:4576-4579 (2013)) were prepared according to literature procedures. 3a was re-purified by sublimation twice under high vacuum. All liquid alkynes or diazenes were freeze pump-thawed three times, brought into the glove box and passed through activated basic alumina before being stored at −35° C. $^1H$, $^{13}C$, $^{15}N$, HMBC, HSQC, and No-D NMR spectra were recorded on Varian INOVA 300 MHz or 500 MHz or Bruker Avance III 500 MHz or Bruker Avance III HD 500 MHz spectrometers. Chemical shifts are reported with respect to residual protio-solvent impurity for $^1H$ (s, 7.16 ppm for $C_6D_5H$; s, 7.27 for ppm $CHCl_3$; t, 5.31 for $CHDCl_2$), solvent carbons for $^{13}C$ (t, 128.39 ppm for $C_6D_6$; t, 77.23 ppm for $CDCl_3$; p, 54.00 ppm for $CD_2Cl_2$). No-D NMR spectrum were referenced to the triphenylmethane peak ($Ph_3C$—H, ppm=5.0) at a delay time=30 and acquisition time=5 unless otherwise specified.

1. Solvent Scope Experiments:

To a 20 mL scintillation vial was added 5 mg $(py)_3TiCl_2$(NTolyl) (0.1 eq, 0.0109 mmol), 19.8 mg azobenzene (1 eq, 0.109 mmol), 73.8 μL 3-hexyne (6 eq, 53.39 mg, 0.65 mmol) and 2 mL solvent (Table 3). The reaction was then sealed and heated to the desired temperature (Table 3) for 16 hours. The sample was taken and analyzed by GC-MS for consumption of azobenzene.

TABLE 3

Solvent Scope for Pyrrole Synthesis

| Entry | Solvent | Temp (° C.) | GC-MS Conversion (%) |
|---|---|---|---|
| 1 | fluorobenzene | 80 | 18 |
| 2 | benzene | 80 | <1 |
| 3 | toluene | 110 | 50 |
| 4 | trifluorotoluene | 110 | 99 |
| 5 | p-chlorotoluene | 110 | 90 |
| 6 | THF | 80 | <1 |
| 7 | 1,4-dioxane | 110 | <1 |

2. Catalyst Loading Experiments:

To a 20 mL scintillation vial was added 39.6 mg azobenzene (1 eq, 0.217 mmol), 146 μL 3-hexyne (5 eq, 1.08 mmol), 0.5-10 mol % $(py)_3TiCl_2$(NTolyl), and 4 mL TFT (Table 4). The reaction was then sealed and heated to 110° C. for 16 hours. The sample was then taken and analyzed by GC-MS for consumption of azobenzene.

TABLE 4

Catalyst Loading Optimization

| Entry | mol % Catalyst | GC-MS Conversion (%) |
|---|---|---|
| 1 | 0.5 | 0 |
| 2 | 1 | 0 (53)$^a$ |
| 3 | 2.5 | 82 |
| 4 | 5 | 93 |
| 5 | 10 | 99 |

$^a$Samples run with 1% catalyst loading at double the concentration (118 mg azobenzene, 346.8 μL 3-hexyne, 3 mg $(py)_3TiCl_2$(NTolyl) in 4 mL TFT) led to 53% conversion.

3. Control Reactions:

Under standard conditions, reacting azobenzene and 3-hexyne in the absence of catalyst led to no product formation or azobenzene consumption. Furthermore the reaction of stoichiometric 3-hexyne with $(py)_3TiCl_2$(NPh) led only to trace pyrrole formation.

Under optimized catalytic conditions, the following substrates yielded no reaction:

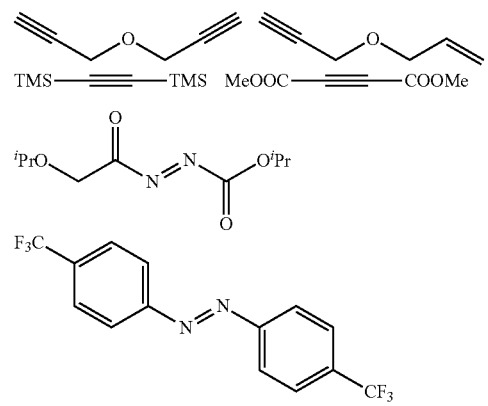

It is possible that in the case of ethers and esters, the Lewis basic functional groups coordinate to Ti and prevent [2+2] cycloaddition from occurring. In the case of $TMS_2C_2$, the reaction temperatures are likely too low for [2+2] cycloaddition to occur.

It has been observed that many of the electron rich-pyrroles synthesized are air sensitive and decompose in solution and on silica/alumina during chromatography. Because of this, some of the pyrroles were not separated from alkyne trimer byproducts. In cases where the pyrroles were not isolated, yields were determined by No-D NMR experiments (Section 5) or by simple H₂O quenches followed by NMR analysis.

4. Pyrrole Syntheses, Isolation and Characterization:

4a. Preparation of 2,3,4,5-tetraethyl-1-phenyl-1H-pyrrole (4a) (Liao et al., *Eur. J. Org. Chem.* 2010:5327-5508 (2010)):

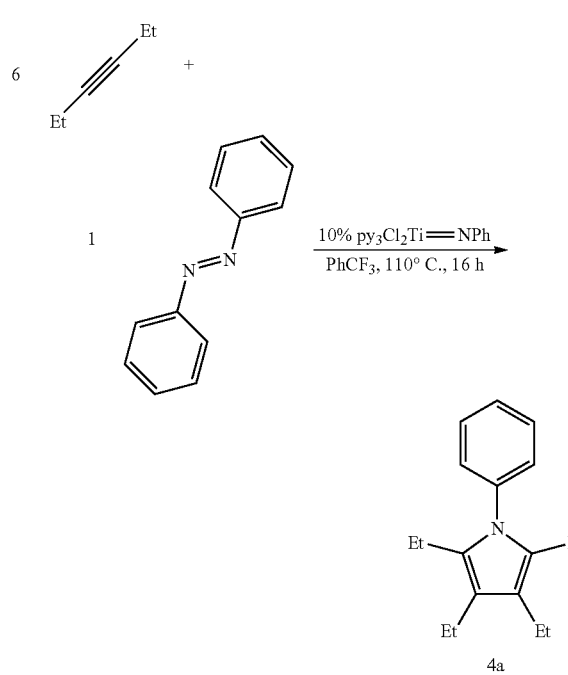

To a 20 mL scintillation vial was added 8.9 mg (py)₃TiCl₂ (NPh) (0.1 eq, 0.0200 mmol), 36.7 mg azobenzene (1 eq, 0.201 mmol), 137.18 μL 3-hexyne (6 eq, 99.05 mg, 1.21 mmol) and 1 mL trifluorotoluene (TFT). The reaction was then sealed and heated to 110° C. for 16 hours and monitored by No-D NMR. The reaction was then quenched with a 50/50 mixture of DCM/H₂O. The organic layer was then washed 2× with H₂O, 1× with brine, dried over MgSO₄, filtered, and concentrated to yield a yellow oil of 4a (92.2 mg, 85.3% yield).

¹H NMR (500 MHz, CDCl₃; δ, ppm): 0.846 (t, J=7.49 Hz, 6H, 3,4-CH₂CH₃); 1.176 (t, J=7.55 Hz, 6H, 2,5-CH₂CH₃); 2.377 (q, J=7.49 Hz, 4H, 2,5-CH₂CH₃); 2.474 (q, J=7.55 Hz, 4H, 3,4-CH₂CH₃); 7.262 (d, J=6.87 Hz, 2H, o-N—C₆H₃—H₂); 7.378 (t, J=7.31 Hz, 1H, p-N—C₆H₄—H); 7.431 (t, J=7.28, 2H, m-N—C₆H₃—H₂).

4b. Preparation of 2,3,4,5-tetramethyl-1-phenyl-1H-pyrrole (4b) (Fang et al., *Chem. Eur. J.* 10:3444-3450 (2004)):

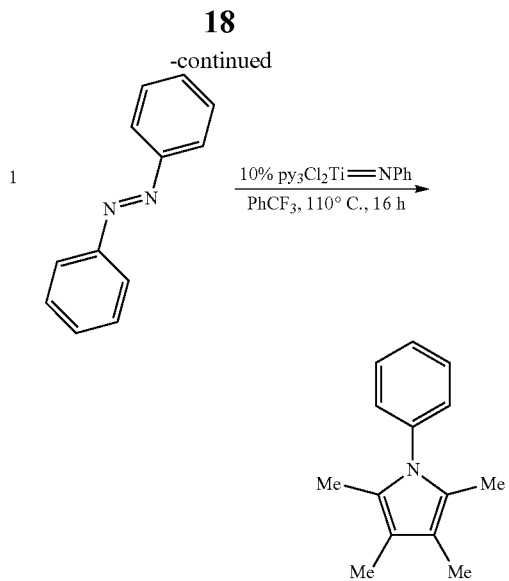

To a 20 mL scintillation vial was added 8.7 mg (py)₃TiCl₂ (NPh) (0.1 eq, 0.0195 mmol), 38.3 mg azobenzene (1 eq, 0.210 mmol), 89.8 μL 2-butyne (6 eq, 62.1 mg, 1.14 mmol) and 1 mL trifluorotoluene (TFT). The reaction was then sealed and heated to 110° C. for 16 hours, and monitored by No-D NMR. The reaction was then quenched with a 50/50 mixture of DCM/H₂O. The organic layer was then washed 2× with H₂O, 1× with brine, dried over MgSO₄, filtered, and concentrated to yield a yellow oil of 4b (64.2 mg, 76% yield).

¹H NMR (500 MHz, CDCl₃; δ, ppm): 1.966 (s, 6H, 2,5-CH₃); 2.016 (s, 6H, 3,4-CH₃); 7.189 (d, J=7.18 Hz, 2H, o-N—C₆H₃—H₂); 7.365 (t, J=7.41 Hz, 1H, p-N—C₆H₄—H); 7.441 (t, J=7.52 Hz, 2H, m-N—C₆H₃—H₂).

4c. Preparation of 1,2,3,4,5-pentaphenyl-1H-pyrrole (4c) (Feng et al., *J. Phys. Chem. B* 50:16731-16736 (2010)):

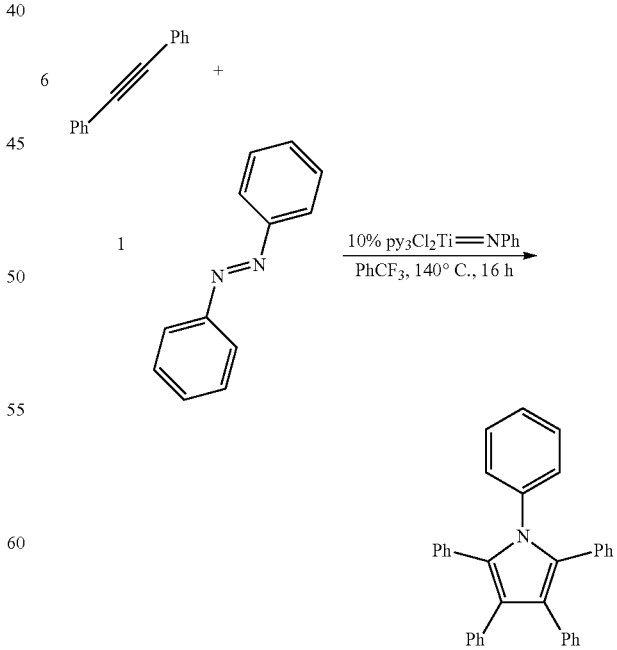

To a 20 mL scintillation vial was added 8.5 mg (py)₃TiCl₂ (NPh) (0.1 eq, 0.0191 mmol), 40.7 mg azobenzene (1 eq, 0.191 mmol), 203 mg diphenylacetylene (6 eq, 1.14 mmol) and 1 mL trifluorotoluene (TFT). The reaction was then sealed and heated to 140° C. for 32 hours, and monitored by No-D NMR. The reaction was then quenched with a 50/50 mixture of DCM/H$_2$O. The organic layer was then washed 2× with H$_2$O, 1× with brine, dried over MgSO$_4$, filtered, and concentrated. The green residue was then sonicated with EtOAc, and the solid precipitate was cooled to yield an off-white solid of 4c (54.7 mg, 25.8% yield).

$^1$H NMR (500 MHz, CD$_2$Cl$_2$; δ, ppm): 6.926-6.966 (m, 10H), 7.049-7.166 (m, 15H).

$^{13}$C NMR (126 MHz; CD$_2$Cl$_2$; δ, ppm): 139.0, 135.9, 132.7, 132.1, 131.7, 131.3, 129.6, 128.5, 127.83, 127.81, 127.3, 126.9, 125.8, 123.2.

4d. Preparation of 2,5-diisopropyl-3,4-dimethyl-1-phenyl-1H-pyrrole (4d); 2,4-diisopropyl-3,5-dimethyl-1-phenyl-1H-pyrrole (5d); 3,4-diisopropyl-2,5-dimethyl-1-phenyl-1H-pyrrole (6d):

a 50/50 mixture of DCM/H$_2$O. The organic layer was then washed 2× with H$_2$O, 1× with brine, dried over MgSO$_4$, filtered, and concentrated to an orange sticky solid as a mixture of the title compounds. The reaction mixture was then purified by column chromatography (100% Hexanes) to yield a mixture of the 3 regioisomers (32.2 mg yield pyrrole, 30.40% yield). The product mixture ratio was determined by $^1$H-$^{13}$C and $^1$H-1-$^{13}$C HMBC.

GC-HRMS (m/z): calcd. for C$_{18}$H$_{25}$N, 255.1987; found, 255.1981.

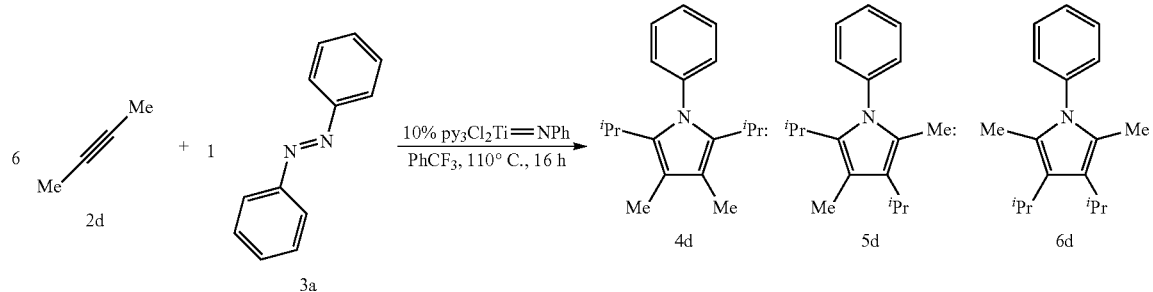

To a 20 mL scintillation vial was added 8.6 mg (py)$_3$TiCl$_2$(NPh) (0.1 eq, 0.019 mmol), 36.10 mg azobenzene (1 eq, 0.198 mmol), 69.9 mg 4-methylpent-2-yne (6 eq, 0.831 mmol) and 1 mL trifluorotoluene (TFT). The reaction was then sealed and heated to 110° C. for 16 hours, and monitored by No-D NMR. The reaction was then quenched with 4e. Preparation of 3,4-dimethyl-1,2,5-triphenyl-1H-pyrrole (4f); 2,4-dimethyl-1,3,5-triphenyl-1H-pyrrole (5f); 2,5-dimethyl-1,3,4-triphenyl-1H-pyrrole(6f):

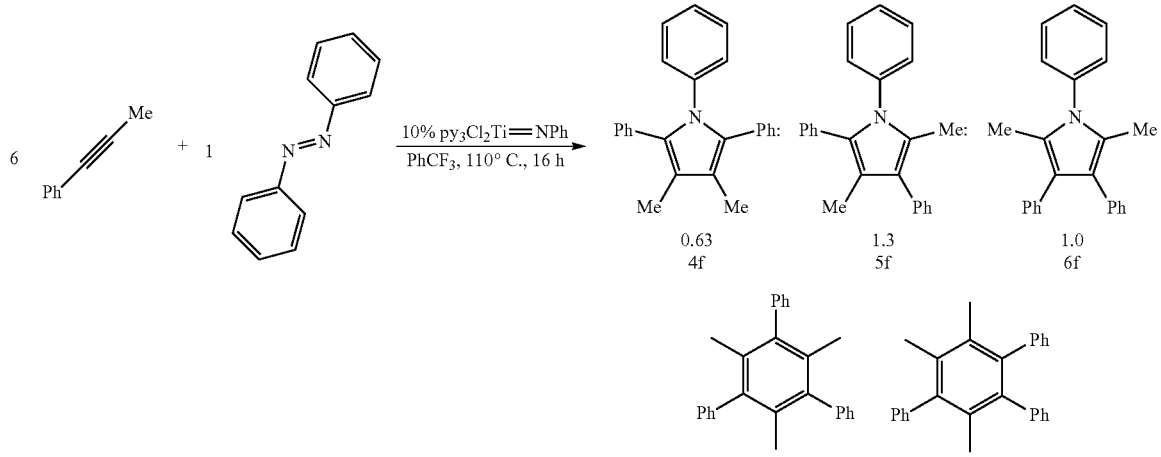

To a 20 mL scintillation vial was added 8.6 mg (py)$_3$TiCl$_2$(NPh) (0.1 eq, 0.019 mmol), 35.0 mg azobenzene (1 eq, 0.192 mmol), 143.6 μL 1-phenylpropyne (6 eq, 133.3 mg, 1.15 mmol) and 1 mL trifluorotoluene (TFT). The reaction was then sealed and heated to 110° C. for 16 hours, and monitored by No-D NMR. The reaction was then quenched with a 50/50 mixture of DCM/H$_2$O. The organic layer was then washed 2× with H$_2$O, 1× with brine, dried over MgSO$_4$, filtered, and concentrated to yield an off-yellow sticky solid as a mixture of the title compounds (74 mg yield pyrrole, 59.8% yield). The product mixture ratio was determined by $^1$H-$^{13}$C and $^1$H-$^{15}$N HMBC.

GC-HRMS (m/z): calcd. for C$_{23}$H$_{21}$N, 323.1674; found, 323.1662, 323.1666, 323.1668.

4f. Preparation of 1,2,4-triphenyl-1H-pyrrole (5g) (Thompson et al., *Org. Lett.* 13:3289-3291 (2011)); 1,3,4-triphenyl-1H-pyrrole (6g) (Li et al., *Org. Lett.* 12:4066-4069 (2010)):

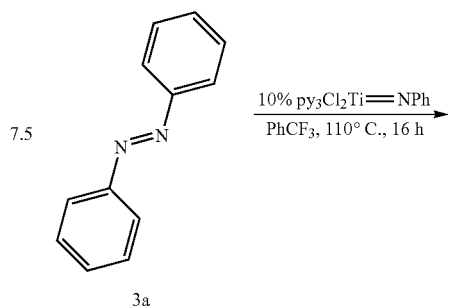

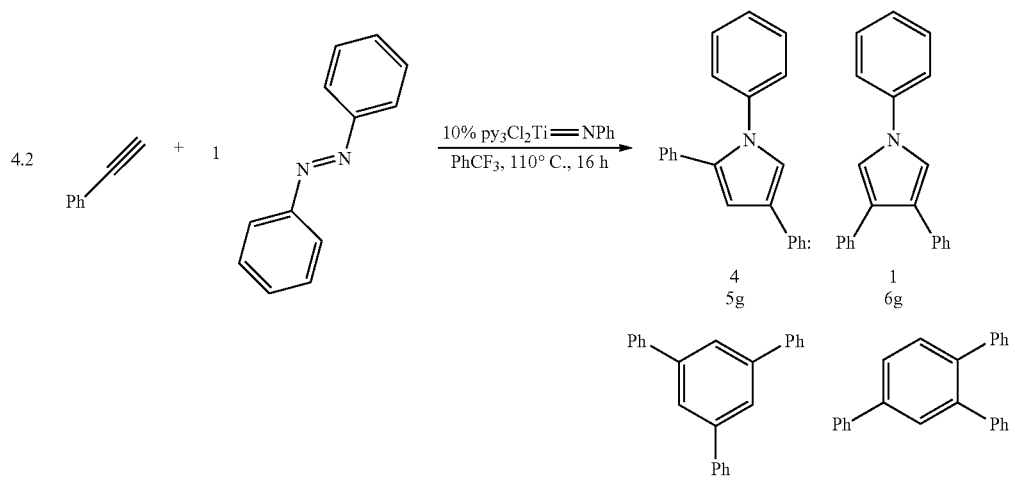

To a 10 mL round bottom flask was added 17 mg (py)$_3$TiCl$_2$(NPh) (0.1 eq, 0.038 mmol) and 71.5 mg azobenzene (1 eq, 0.392 mmol) and 1 mL TFT. The reaction mixture was then heated to 110° C. To this was added 175.9 μL phenylacetylene (4.2 eq, 1.60 mmol as a solution in 1 mL TFT containing 0.19 M triphenylmethane) dropwise at a rate of 0.1 mL every 20 minutes until complete addition. The reaction was then left to stir at 110° C. for 16 hours, and then quenched with a 50/50 mixture of DCM/H$_2$O. The organic layer was then washed 2× with H$_2$O, 1× with brine, dried over MgSO$_4$, filtered, and concentrated to yield a light orange solid as a (4:1) mixture of 4j and 4k (32.4% yield by NMR). Ratio based on $^{13}$C-IG NMR with a delay time=20, at=2, and nt=1024.

4g. Preparation of 2,4-di-n-butyl-1-phenyl-1H-pyrrole (5h):

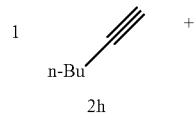

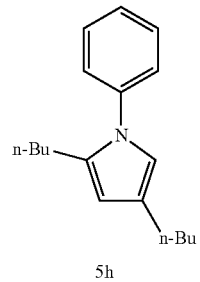

To a 20 mL scintillation vial was added 9 mg (py)$_3$TiCl$_2$(NPh) (0.05 eq, 0.019 mmol), 262.0 mg azobenzene (7.5 eq, 1.437 mmol), 29.28 mg 1-hexyne (1 eq, 0.357 mmol) and 1 mL trifluorotoluene (TFT). The reaction was then sealed and heated to 110° C. for 16 hours, and monitored by No-D NMR. The reaction was then concentrated taken up on minimal hexanes and purified by column chromatography using 100% hexanes to give a clear oil of the title compound (16.3 mg, 35.8% yield).

$^1$H NMR (500 MHz, CDCl$_3$; δ, ppm): 0.824 (t, J=7.35 Hz, 3H, —CH$_2$CH$_3$), 0.936 (t, J=7.35 Hz, 3H, —CH$_2$CH$_3$), 1.286 (sex, J=7.41 Hz, 2H—CH$_2$CH$_2$CH$_3$), 1.404 (sex, J=7.41 Hz, 2H—CH$_2$CH$_2$CH$_3$), 1.496 (p, J=7.66, 2H, —CH$_2$CH$_2$CH$_3$), 1.585 (p, J=7.66, 2H, —CH$_2$CH$_2$CH$_3$), 2.476 (t, J=6.8 Hz, 2H, NC$_4$H$_2$—CH$_2$CH$_3$—) 2.503 (t, J=6.8 Hz, 2H, NC$_4$H$_2$—CH$_2$CH$_3$—), 5.928 (d, J=1.83 Hz, 1H, 3-HC₄NH), 6.514 (d, J=1.91 Hz, 1H, 5-HC₄NH), 7.291 (m, 3H, o,p-N—C₆H₂—H₃), 7.409 (m, 3H, m-N—C₆H₂—H₃).

$^{13}$C NMR (125 MHz, CDCl₃; δ, ppm): 14.029, 14.192, 22.641, 22.858, 26.676, 26.858, 31.449, 33.303, 107.482, 118.562, 124.502, 126.038, 126.647, 129.038, 133.998, 140.770.

GC-HRMS (m/z): calcd. for $C_{18}H_{25}N$, 255.1987; found, 253.1986 and 255.1983.

4h. Preparation of 2,4-di-tert-butyl-1-phenyl-1H-pyrrole (5i):

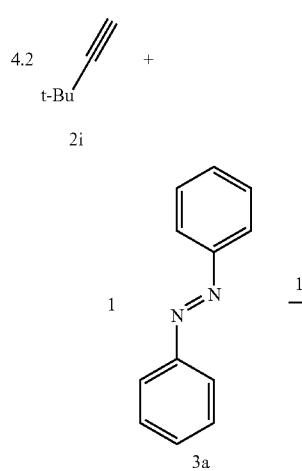

To a 20 mL scintillation vial was added 8.8 mg $(py)_3TiCl_2$(NPh) (0.1 eq, 0.019 mmol), 36.10 mg azobenzene (1 eq, 0.198 mmol), 65.71 mg 3,3-dimethylbut-1-yne (4.2 eq, 0.832 mmol) and 1 mL trifluorotoluene (TFT). The reaction was then sealed and heated to 110° C. for 16 hours, and monitored by No-D NMR. The reaction was then concentrated taken up on minimal hexanes and purified by column chromatography using 100% hexanes to give a clear oil of the title compound (55.6 mg, 55% yield).

$^1$H NMR (500 MHz, CDCl₃; δ, ppm): 1.149 (s, 9H, 4-tBu), 1.255 (s, 9H, 2-tBu), 5.955 (d, J=2.13 Hz, 1H, 3-HC₄NH), 6.296 (d, J=2.15 Hz, 1H, 5-HC₄NH), 7.381 (m, 5H, N—C₆H₅).

$^{13}$C NMR (125 MHz, CDCl₃; δ, ppm): 31.352, 31.510, 31.830, 31.830, 103.546, 119.794, 127.774, 128.193, 129.347, 133.024, 142.895, 143.214.

GC-HRMS (m/z): calcd. for $C_{18}H_{25}N$, 255.1987; found, 255.1983.

4i. Preparation of 1,2,3-triphenyl-2,4,5,6-tetrahydrocyclopenta[c]pyrrole (4l):

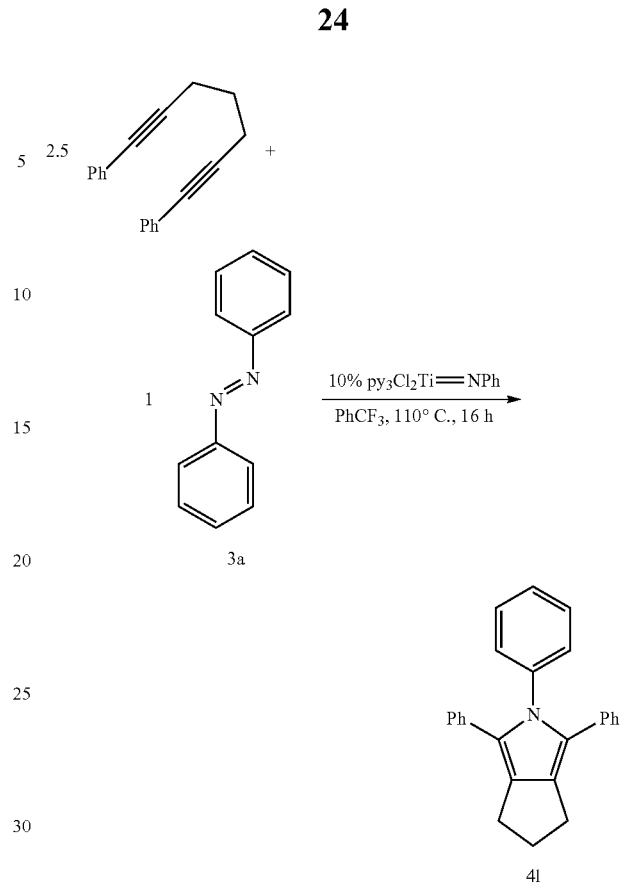

To a 20 mL scintillation vial was added 8.8 mg $(py)_3TiCl_2$(NPh) (0.1 eq, 0.019 mmol), 36.10 mg azobenzene (1 eq, 0.198 mmol), 122.1 mg 1,7-diphenylhepta-1,6-diyne (2.5 eq, 0.495 mmol) and 1 mL trifluorotoluene (TFT). The reaction was then sealed and heated to 110° C. for 16 hours, and monitored by No-D NMR. The precipitate was then filtered from the crude reaction mixture, washed with hexanes to give the title compound as a tan solid (60.0 mg, 46.36% yield).

$^1$H NMR (500 MHz, CDCl₃; δ, ppm): 2.459 (p, J=7.16 Hz, 2H, C₅H₄—H₂) 2.897 (t, J=7.17 Hz, 4H, C₅H₂—H₄), 7.125 (m, 15H, Aryl).

$^{13}$C NMR (125 MHz, CDCl₃; δ, ppm): 26.123, 30.808, 125.479, 126.156, 126.811, 127.796, 128.633, 128.698, 129.044, 131.183, 133.252, 139.631.

GC-HRMS (m/z): calcd. for $C_{25}H_{21}N$, 355.1674; found, 355.1664.

4j. Preparation of 1,3-diethyl-2-phenyl-4,5,6,7-tetrahydro-2H-isoindole (4m):

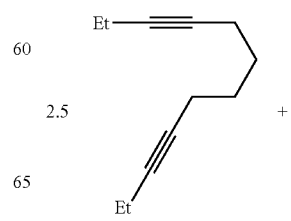

-continued

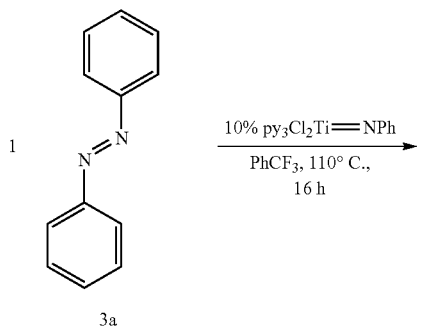
3a

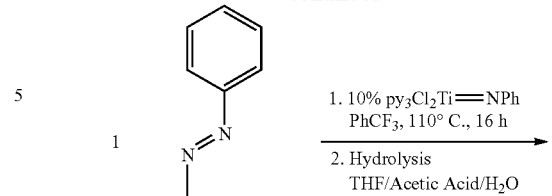

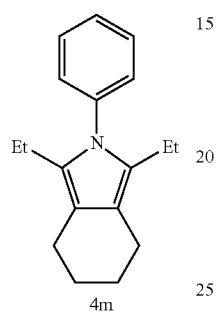
4m

To a 20 mL scintillation vial was added 8.8 mg (py)$_3$TiCl$_2$(NPh) (0.1 eq, 0.019 mmol), 36.10 mg azobenzene (1 eq, 0.198 mmol), 80.32 mg dodeca-3,9-diyne (2.2 eq, 0.436 mmol) and 1 mL trifluorotoluene (TFT). The reaction was then sealed and heated to 110° C. for 16 hours, and monitored by No-D NMR. The reaction was then concentrated taken up on minimal hexanes and purified by column chromatography using 100% hexanes to give a clear oil of the title compound (65 mg, 64.78% yield).

$^1$H NMR (500 MHz, CDCl$_3$; δ, ppm): 0.966 (d, J=7.63 Hz, 6H, —CH$_2$CH$_3$), 1.878 (m, 4H, C$_6$H$_4$—H$_4$) 2.443 (q, J=7.56 Hz, 4H, —CH$_2$CH$_3$) 2.650 (m, 4H, C$_6$H$_4$—H$_4$) 7.342 (d, J=7.75 Hz, 2H, o-N—C$_6$H$_3$—H$_2$), 7.453 (t, J=6.89 Hz, 1H, p-N—C$_6$H$_4$—H) 7.508 (t, J=7.67 Hz, 2H, m-N—C$_6$H$_3$—H$_2$).

$^{13}$C NMR (125 MHz, CDCl$_3$; δ, ppm): 14.562, 18.157, 21.783, 24.250, 114.942, 127.463, 128.575, 128.806, 128.930, 139.386.

GC-HRMS (m/z): calcd. for C$_{18}$H$_{23}$N, 253.1830; found, 253.1824.

4k. Preparation of 1-(2-methylcyclopent-1-en-1-yl)pentan-1-one (4n) (Krafft et al., *J. Am. Chem. Soc.* 118:6080-6081 (1996)):

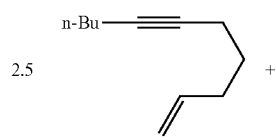

-continued

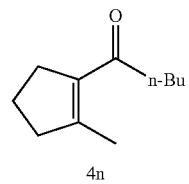
3a

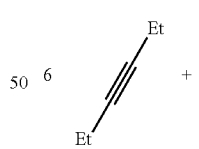
4n

To a 20 mL scintillation vial was added 19.0 mg (py)$_3$TiCl$_2$(NPh) (0.1 eq, 0.042 mmol), 83.8 mg azobenzene (1 eq, 0.460 mmol), 160.8 mg dodec-1-en-7-yne (2.1 eq, 0.985 mmol) and 2 mL trifluorotoluene (TFT). The reaction was then sealed and heated to 110° C. for 16 hours. The reaction was then concentrated in vacuo to a brown sticky oil and then diluted with 10 mL THF. To this was added acetic acid (2.5 mL) and DI H$_2$O (1 mL) and left to stir overnight at room temperature (20 h). The reaction mixture was then diluted with 25 mL EtOAc, washed with H$_2$O (50 mL×2) and NaHCO$_3$ (50 mL). The organic layer was then dried over MgSO$_4$, filtered, and concentrated. The crude orange mixture was purified by column chromatography (neutral alumina) using hexanes as eluent to give a light yellow oil of the title compound (77 mg, 49.9% yield).

$^1$H NMR (500 MHz, CDCl$_3$; δ, ppm): 0.922 (t, J=7.4 Hz, 3H, CH$_2$CH$_3$); 1.34 (sex, J=7.47 2H, CH$_2$CH$_3$); 1.59 (p, J=7.49, 2H, CCH$_2$CH$_2$CH$_2$C); 1.83 (p, J=7.55 Hz, 2H, CH$_2$CH$_2$CO); 2.08 (s, 3H, CCH$_3$); 2.49 (m, 4H, CH$_2$CO & CH$_2$CCH$_3$); 2.67 (t, J=6.38, 2H, CH$_2$CCO)

4l. Preparation of 2,3,4,5-tetraethyl-1-(p-tolyl)-1H-pyrrole (4ab) (Fang et al., *Chem. Eur. J.* 10:3444-3450 (2004)):

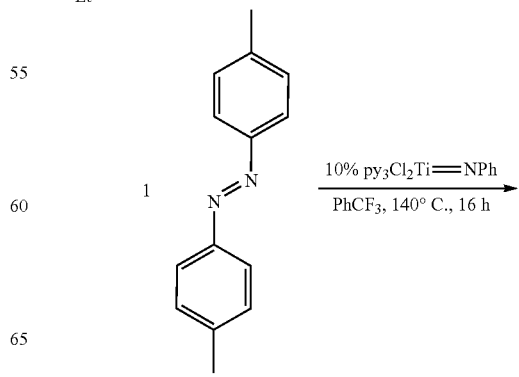

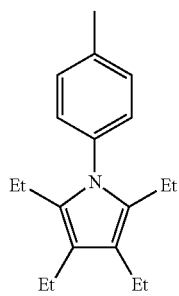

To a 20 mL scintillation vial was added 8.5 mg (py)$_3$TiCl$_2$ (NPh) (0.1 eq, 0.0191 mmol), 40.7 mg 1,2-di-p-tolyldiazene (1 eq, 0.191 mmol), 129.8 μL 3-hexyne (6 eq, 93.88 mg, 1.14 mmol) and 1 mL trifluorotoluene (TFT). The reaction was then sealed and heated to 140° C. for 16 hours, and monitored by No-D NMR. The reaction was then quenched with a 50/50 mixture of DCM/H$_2$O. The organic layer was then washed 2× with H$_2$O, 1× with brine, dried over MgSO$_4$, filtered, and concentrated to yield a yellow oil of 4ab (88.6 mg, 85% yield).

$^1$H NMR (500 MHz, CDCl$_3$; δ, ppm): 0.854 (t, J=7.5 Hz, 6H, 3,4-CH$_2$CH$_3$); 1.170 (t, J=7.55 Hz, 6H, 2,5-CH$_2$CH$_3$); 2.364 (q, J=7.49 Hz, 4H, 2,5-CH$_2$CH$_3$); 2.416 (s, 3H, p-CH$_3$); 2.467 (q, J=7.55 Hz, 4H, 3,4-CH$_2$—CH$_3$); 7.136 (d, J=8.21 Hz, 2H, o-N—C$_6$H$_2$—H$_2$); 7.220 (d, J=7.92 Hz, 2H, m-N—C$_6$H$_2$—H$_2$).

4m. Preparation of 2,3,4,5-tetraethyl-1-(o-tolyl)-1H-pyrrole (4ac):

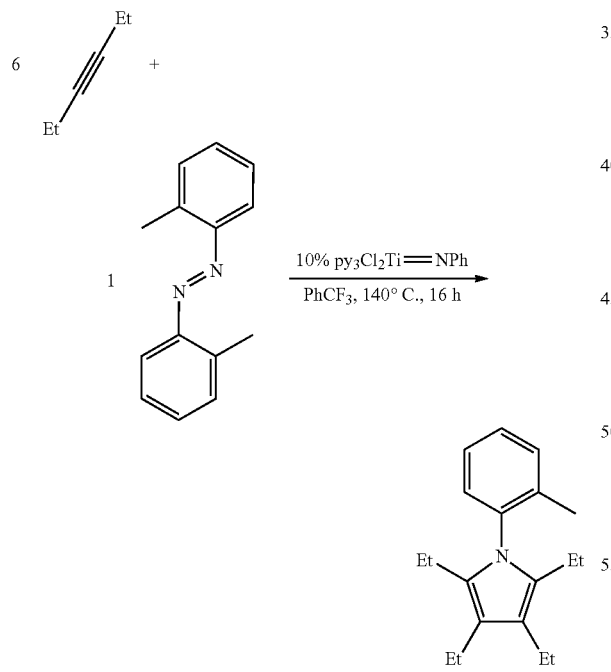

To a 20 mL scintillation vial was added 8.5 mg (py)$_3$TiCl$_2$ (NPh) (0.1 eq, 0.0191 mmol), 40.2 mg 1,2-di-o-tolyldiazene (1 eq, 0.191 mmol), 129.8 μL 3-hexyne (6 eq, 93.88 mg, 1.14 mmol) and 1 mL trifluorotoluene (TFT). The reaction was then sealed and heated to 140° C. for 16 hours, and monitored by No-D NMR. The reaction was then quenched with a 50/50 mixture of DCM/H$_2$O. The organic layer was then washed 2× with H$_2$O, 1× with brine, dried over MgSO$_4$, filtered, and concentrated to yield a dark yellow oil of 4ac (79 mg, 70.6% yield).

$^1$H NMR (500 MHz, CDCl$_3$; δ, ppm): 0.831 (t, J=7.5 Hz, 6H, 3,4-CH$_2$CH$_3$); 1.115 (t, J=7.54 Hz, 6H, 2,5-CH$_2$CH$_3$); 1.867 (s, 3H, o-CH$_3$); 2.112 (dq, J=14.83 Hz, 7.43 Hz, 2H, 2,5-CHH—CH$_3$); 2.362 (dq, J=14.83 Hz, 7.43 Hz, 2H, 2,5-CHH—CH$_3$); 2.461 (q, J=7.54 Hz, 4H 3,4-CH$_2$CH$_3$); 7.24-7.31 (m, 4H, Ar).

$^{13}$C NMR (125 MHz, CDCl$_3$; δ, ppm): 15.657, 17.279, 18.003, 18.003, 18.068, 119.446, 126.227, 128.040, 129.303, 129.888, 130.516, 137.868, 138.923.

HRMS (m/z): [M+H]$^+$ calcd. for C$_{19}$H$_{27}$N, 270.2222; found, 270.2228.

4n. Preparation of 2,3,4,5-tetraethyl-1-(4-methoxyphenyl)-1H-pyrrole (4ae) (Fang et al., *Chem. Eur. J.* 10:3444-3450 (2004)):

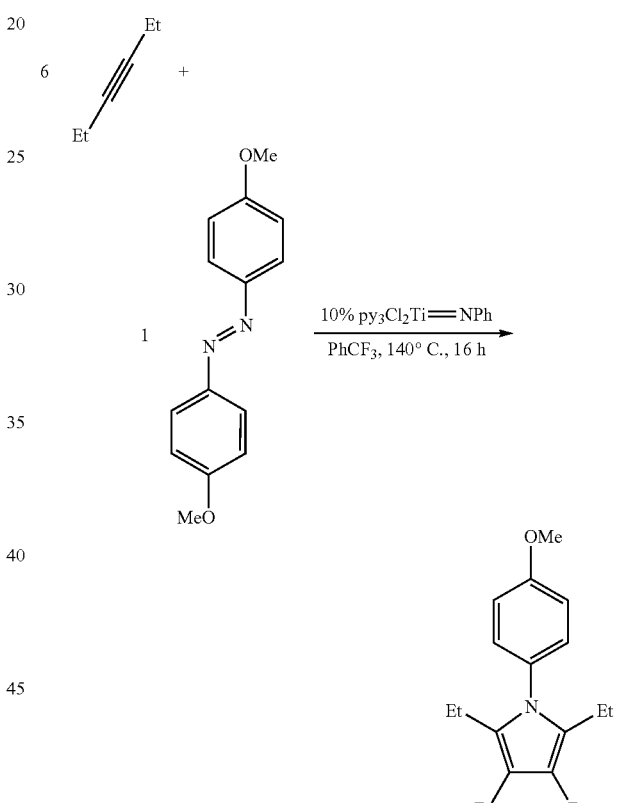

To a 20 mL scintillation vial was added 7.1 mg (py)$_3$TiCl$_2$ (NPh) (0.1 eq, 0.0159 mmol), 38.5 mg 1,2-bis(4-methoxyphenyl)diazene (1 eq, 0.159 mmol), 107.9 μL 3-hexyne (6 eq, 93.88 mg, 1.14 mmol) and 1 mL trifluorotoluene (TFT). The reaction was then sealed and heated to 140° C. for 16 hours, and monitored by No-D NMR. The reaction was then quenched with a 50/50 mixture of DCM/H$_2$O. The organic layer was then washed 2× with H$_2$O, 1× with brine, dried over MgSO$_4$, filtered, and concentrated to yield a dark yellow oil. The oil was then subject to silica column using 100% DCM to yield the title compound as pale yellow oil, 4ae (59.5 mg, 65.6% yield).

$^1$H NMR (500 MHz, CD$_2$Cl$_2$; δ, ppm): 0.82 (t, J=7.5 Hz, 7H), 1.12 (t, J=7.5 Hz, 7H), 2.32 (q, J=7.5 Hz, 5H), 2.42 (q, J=7.5 Hz, 5H), 3.84 (s, 3H), 6.94 (d, J=8.8 Hz, 2H), 7.12 (d, J=8.8 Hz, 2H).

$^{13}$C NMR (125 MHz; CD2Cl2; δ, ppm): 15.81, 17.17, 18.04, 18.11, 55.75, 114.14, 119.37, 130.36, 130.39, 132.44, 159.12.

5. No-D NMR Determination of Reaction Yields:

To a screw cap NMR tube was added 8.5 mg (py)$_3$TiCl$_2$ (NPh) (0.1 eq, 0.0191 mmol), diazene (1 eq, 0.191 mmol), alkyne (6 eq, 1.14 mmol) and 1 mL of a 0.19 M stock solution of triphenylmethane (Internal Standard=I.S.) in TFT, unless otherwise specified. The reaction was then sealed and Initial Time=0 No-D NMR was taken. The reaction was then heated in an oil bath for 16-32 hours at the desired temperature. Afterward, the reaction was cooled to room temperature and a No-D NMR was taken. Spectra were taken using a d1=30, at =5, and nt=8 to allow full relaxation of the I.S (triphenylmethane, Ph$_3$C—H referenced to 5 ppm) on a Varian INOVA 300 MHz NMR. Yields were determined by comparison with I.S.

5a. No-D NMR Reaction of 2a with 3a to Synthesize 4a:

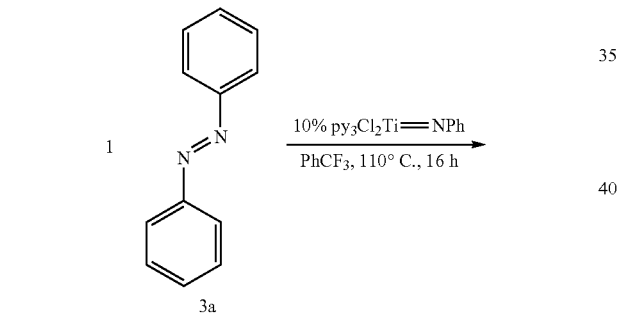

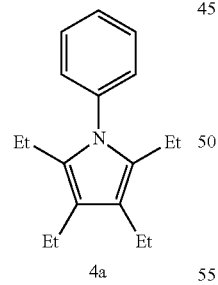

5b. No-D NMR Reaction of 2b with 3a to Synthesize 4b:

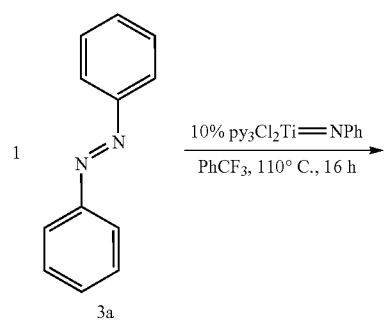

5c. No-D NMR Reaction of 2c with 3a to Synthesize 4c:

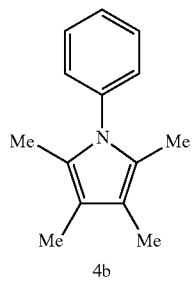

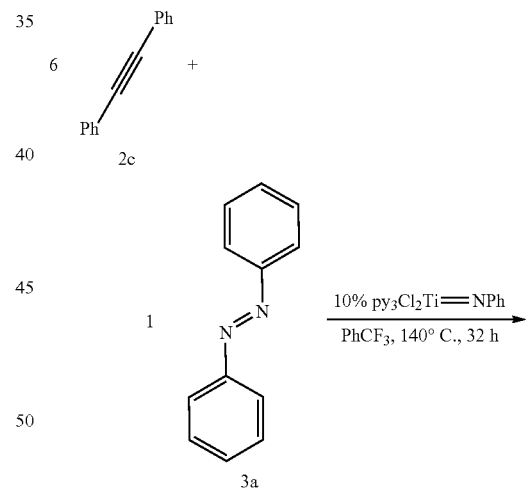

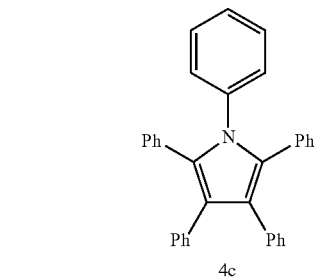

5d. No-D NMR Reaction of 2d with 3a to Synthesize 4d/5d/6d:

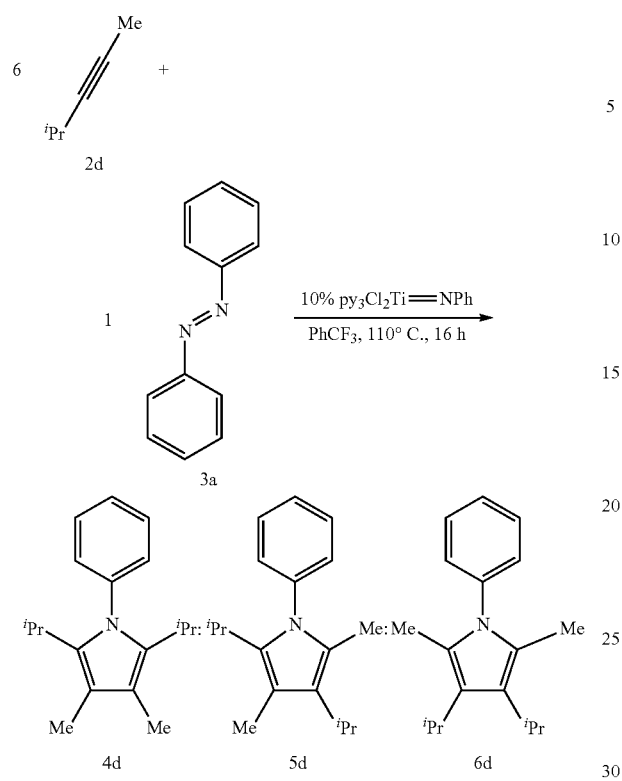
5e. No-D NMR Reaction of 2e with 3a to Synthesis 5e:
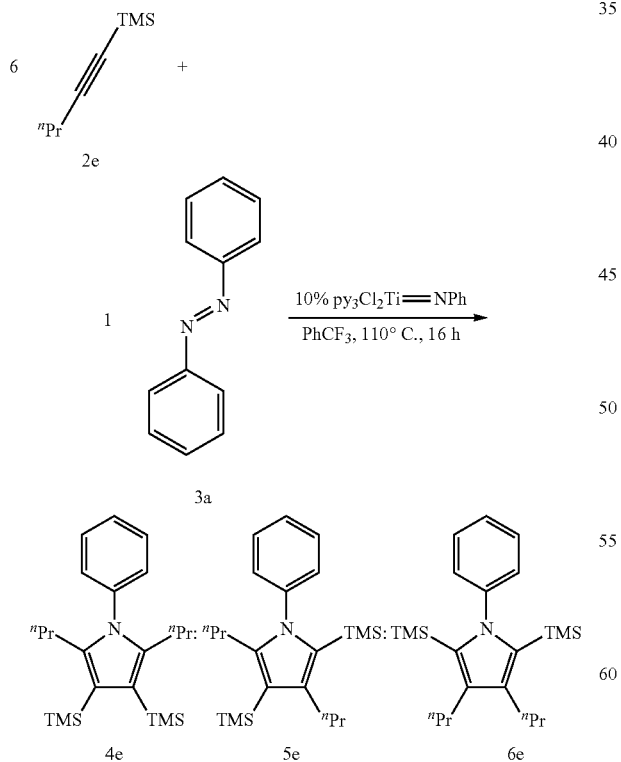
GC-HRMS (m/z): calcd. for $C_{22}H_{37}N_1Si_2$ 371.2465; found, 371.2459.
5f. No-D NMR Reaction of 2f with 3a to Synthesize 4f/5f/5f:
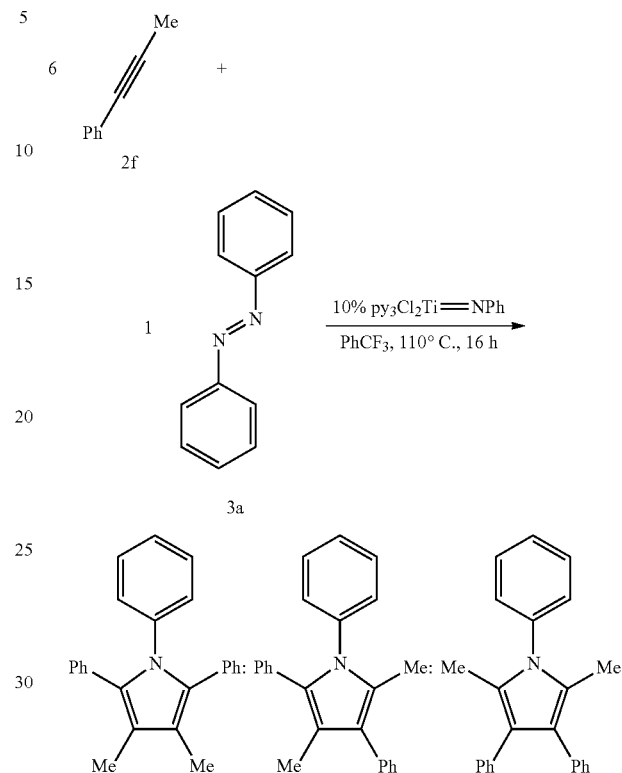
5g. No-D NMR Reaction of 2h with 3a to Synthesize 4h/5h/6h:
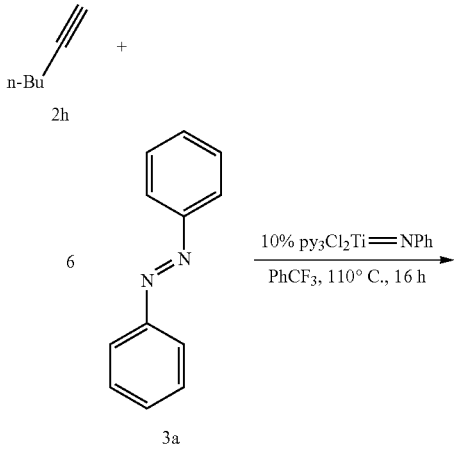

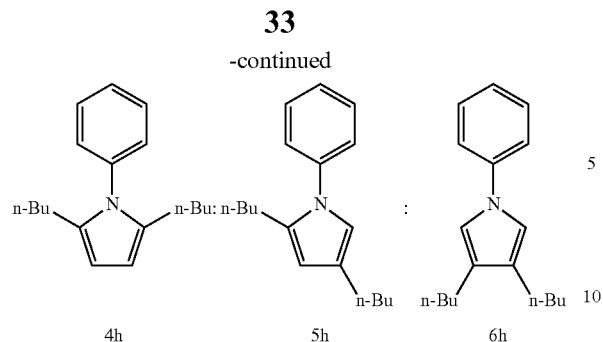

1 eq. of alkyne was used with 6 eq. of 3a to reduce alkyne trimerization.

The crude reaction mixture was transferred to a 20 mL scintillation vial using DCM to aid in the transfer. The reaction mixture was then concentrated to dryness and diluted with CDCl$_3$. The $^1$H-$^{15}$N HMBC, shown below, was used to determine the major product in the No-D NMR.

5h. No-D NMR Reaction of 2i with 3a to Synthesize 5i:

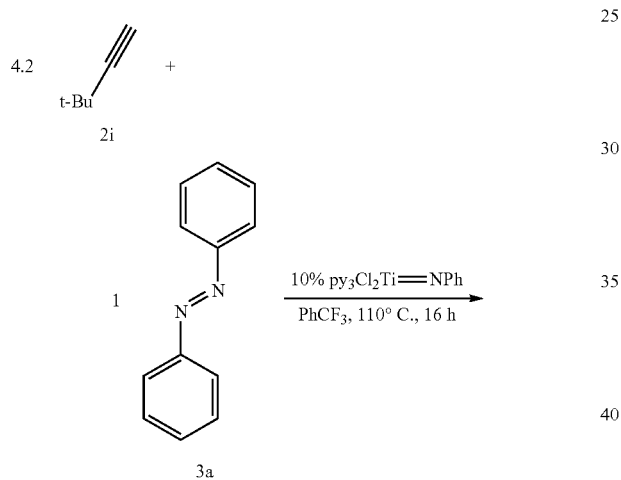

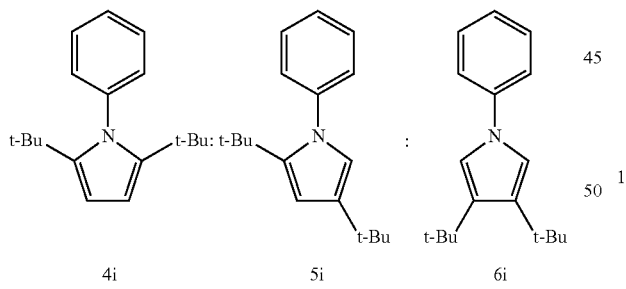

4.2 eq. of alkyne was used.

5i. No-D NMR Reaction of 2j with 3a to Synthesize 4j/5j/6j:

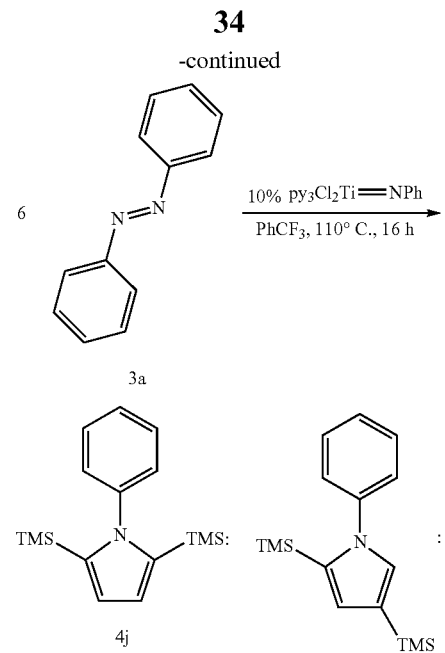

1 eq. of alkyne was used with 6 eq. of 3a to reduce alkyne trimerization.

GC-HRMS (m/z): calcd. for C$_{16}$H$_{25}$NSi$_2$, 287.1526; found, 287.1521 and 287.1520.

5j. No-D NMR Reaction of 2k with 3a to Synthesize 4k:

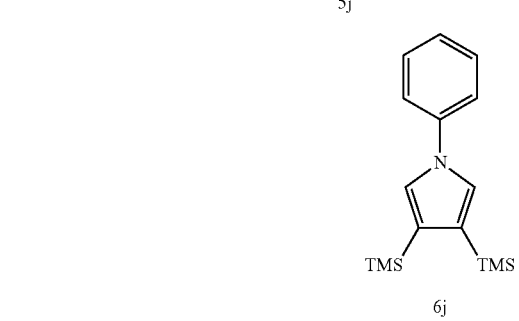

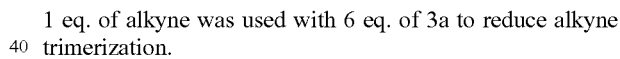

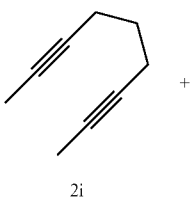

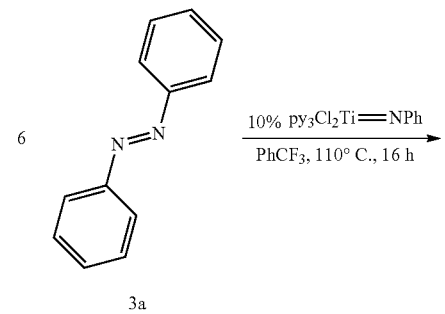

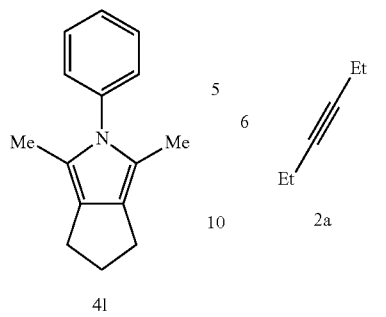
1 eq. of diyne was used with 6 eq. of 3a to reduce alkyne trimerization.
GC-HRMS (m/z): calcd. for $C_{15}H_{17}N$, 211.1361; found, 211.1355.
5k. No-D NMR Reaction of 2m with 3a to Synthesize 4m:
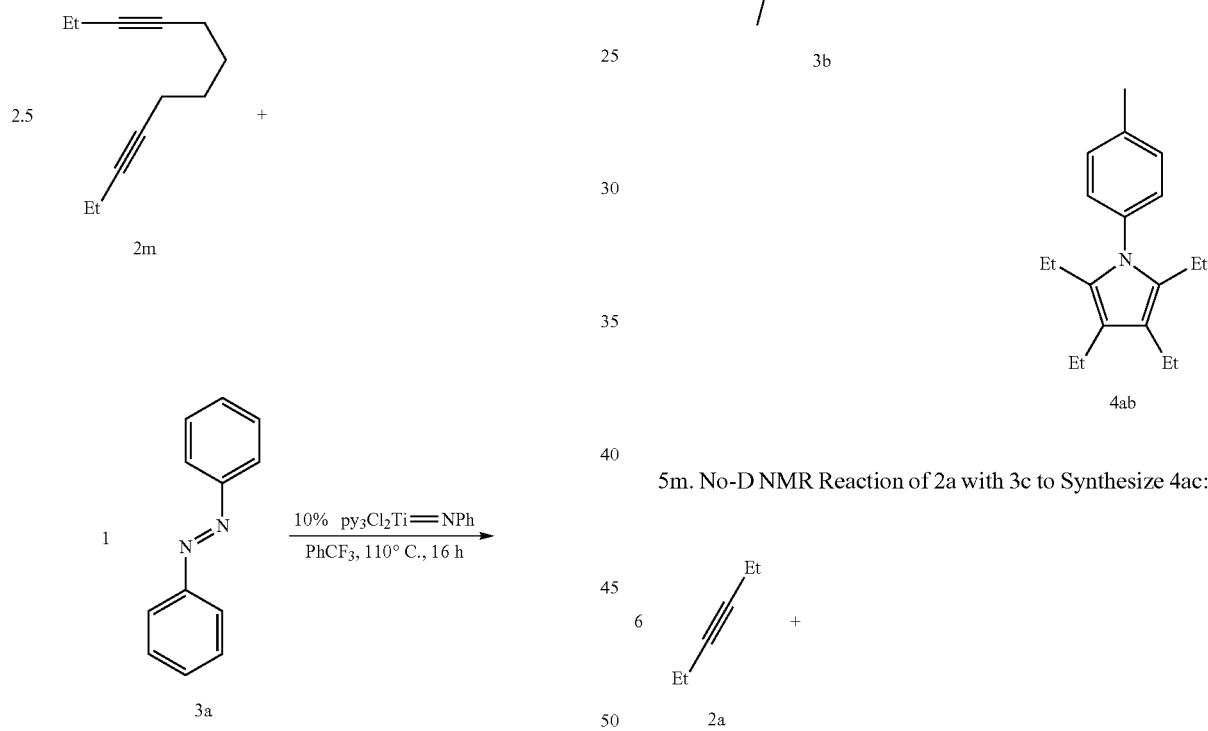
2.5 eq. of alkyne was used.
5l. No-D NMR Reaction of 2a with 3b to Synthesize 4ab:
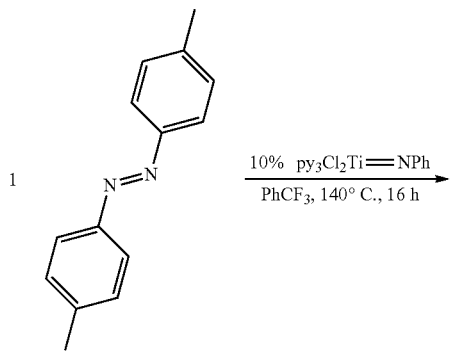
5m. No-D NMR Reaction of 2a with 3c to Synthesize 4ac:
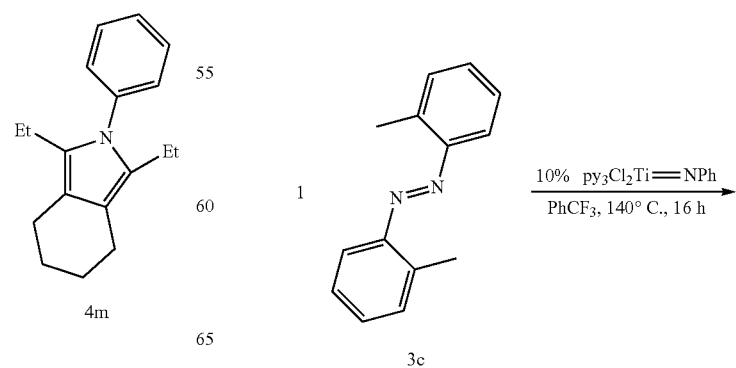

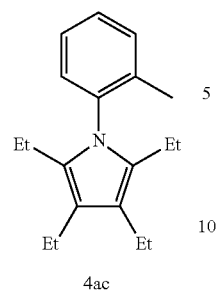
4ac
5n. No-D NMR Reaction of 2a with 3d to Synthesize 4ad:
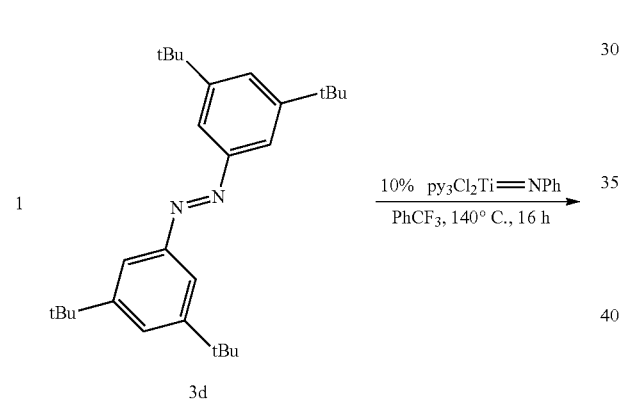
5o. No-D Reaction of 2a with 3e to Synthesize 4ae:
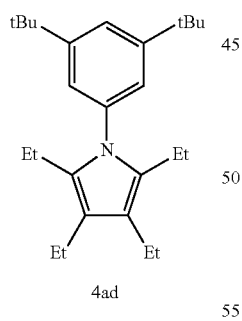
2a
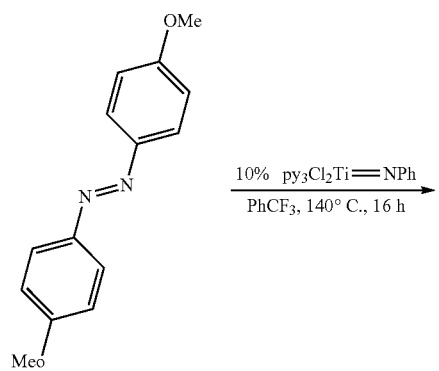
3e
4ae
5p. No-D Reaction of 2a with 3i to Synthesize 4a/4ai:
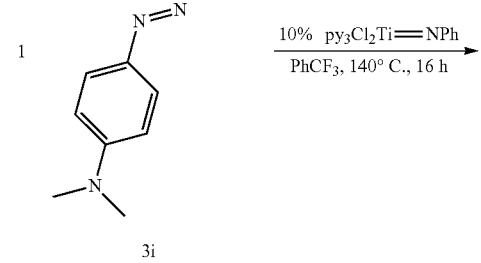

-continued

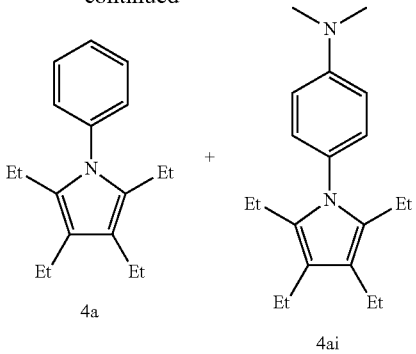

6. Preparation of (PhNNPh)TiCl$_2$(HNMe$_2$) (7):

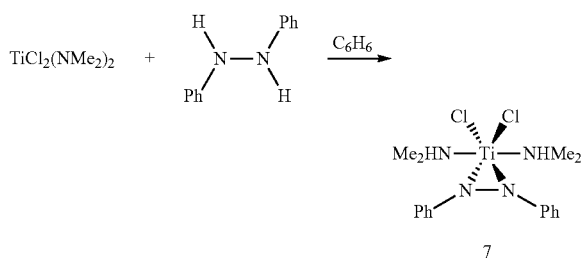

To a 20 mL scintillation vial with stir bar was added 0.100 g TiCl$_2$(NMe$_2$) (0.485 mmol) in 5 mL benzene. To this was added dropwise 0.098 g hydrazobenzene (0.534 mmol, 1.1 eq.) in 5 mL benzene over 5 minutes. The reaction was left to stir overnight at room temperature. The reaction mixture was then concentrated, diluted in hexanes and filtered, washing 2× with hexanes to give 0.135 mg, 70%, of (PhN-NPh)TiCl$_2$(HNMe$_2$)$_2$, 5, as a dark brown/green powder of >95% purity. X-ray-quality crystals were grown from a 50/50 hexanes/toluene solution cooled to −35° C.

$^1$H NMR (300 MHz, C$_6$D$_6$; δ, ppm): 1.71 (br m, 2H, NH(CH$_3$)$_2$); 1.96 (d, J=5.9, 12 H, NH(CH$_3$)$_2$); 6.76 (t, J=6.8 Hz, 2H, 4-C$_6$H$_4$—H); 7.13 (t, J=7.5 Hz, 3,5-C$_6$H$_3$—H$_2$); 7.36 (d, J=7.7 Hz, 2,6-C$_6$H$_3$—H$_2$).

$^{13}$C NMR (125 MHz, C$_6$D$_6$; δ, ppm): 42.194 (HN(CH$_3$)$_2$), 117.787 (2,6-N—C$_6$H$_6$), 122.901 (4-N—C$_6$H$_6$), 129.00 (3,5-N—C$_6$H$_6$), 155.526 (1-N—C$_6$H$_6$).

Elemental analysis (calcd, found; for C$_{16}$H$_{24}$Cl$_2$N$_4$Ti): C (49.13, 49.22), H (6.18, 6.19), N (14.32, 14.21).

7. Synthesis of 2l and 2n:

7a. Synthesis of 1,7-diphenylhepta-1,6-diyne (Lucht et al., *J. Am. Chem. Soc.* 120:4354-4365 (1998)):

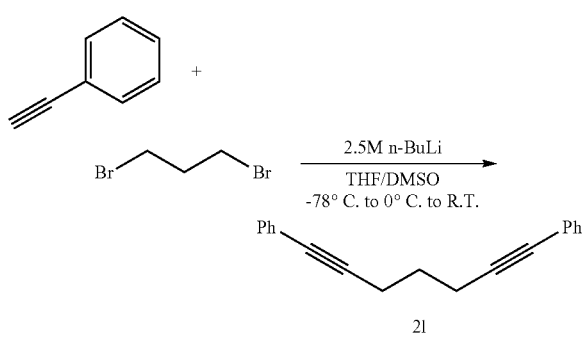

In a glovebox a 50 mL schlenk flask was charged with 10 mL dry THF and 3.34 g phenylacetylene (2 eq, 3.6 mL, 0.0328 mol). The flask was then removed from the glovebox and cooled to −78° C. To this was added 13.10 mL n-BuLi (2eq, 2.5 M in hexanes, 0.0328 mol) dropwise over 30 minutes. The reaction mixture was allowed to warm to room temperature and stirred for 1 hour. To this was added 3.28 g of 1,3 dibromopropane (1 eq, 0.0164 mol) was added dropwise as a solution in dry DMSO (10 mL) at 0° C. and was then left to stir at room temperature overnight. This was then quenched w/ Sat. NH$_4$Cl (50 mL). The aqueous layers were back extracted with hexanes (200 mL), the organic layers were combined, washed with brine, dried over MgSO$_4$, filtered, and concentrated to a yellow oil. The crude mixture was passed through a plug of silica eluting with hexanes. The fractions were the concentrated in vacuo at 50° C. at 5 mmbar to remove all residual phenylacetylene, leaving a clear viscous oil of the title compound (2.2 g, 55% yield).

$^1$H NMR (500 MHz, CDCl$_3$; δ, ppm): 1.921 (p, J=7.01, 2H, —CH$_2$CH$_2$CH$_2$—), 2.607 (t, J=7.01, 4H, —CH$_2$CH$_2$CH$_2$—), 7.29 (m, 6H, Ar), 7.40 (m, 4H, Ar).

7b. Synthesis of undec-1-en-6-yne (Krafft et al., *J. Am. Chem. Soc.* 115:7199-7207 (1993)):

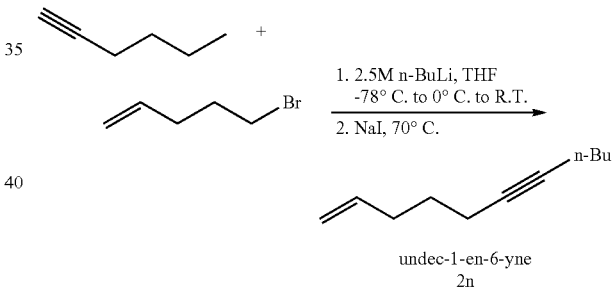

In a glovebox a 50 mL schlenk flask was charged with 40 mL dry THF and 1.06 g 1-hexyne (1.5 eq, 1.48 mL, 0.0129 mol). The flask was then removed from the glovebox and cooled to −78° C. To this was added 5.16 mL n-BuLi (1.5 eq, 2.5 M in hexanes, 0.0129 mol) dropwise over 30 minutes. The reaction mixture was allowed to warm to room temperature and stirred for 1 hour. To this was then added 1.478 g of 5-bromopent-1-ene (1 eq, 0.01 mol) and 74 mg NaI (0.05 eq) and heated to 70° C. over 20 hours. The reaction vessel was then cooled to room temperature quenched with DI H$_2$O (2 mL) then extracted with brine (50 mL). The aqueous layers were back extracted with hexanes (200 mL), the organic layers were combined, washed with brine, dried over MgSO$_4$, filtered, and concentrated to a yellow oil. The crude mixture was passed through a plug of silica eluting with hexanes to give the title compound as a clear and colorless liquid (1.1 g, 73% yield).

$^1$H NMR (500 MHz, CDCl$_3$; δ, ppm): 0.93 (t, J=7.2 Hz, 3H), 1.51-1.40 (m, 4H), 1.60 (p, J=7.3 Hz, 2H), 2.20-2.14 (m, 6H), 4.99 (ddt, J=10.2, 2.1, 1.1 Hz, 1H), 5.05 (dq, J=17.1, 1.8 Hz, 1H), 5.83 (ddt, J=17.0, 10.3, 6.7 Hz, 1H).

8. Hydroamination Reactions:
8a. No-D NMR Hydroamination Reaction of Aniline with 2f:

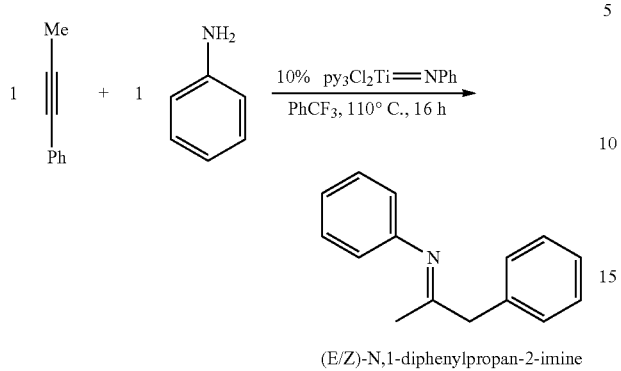

(E/Z)-N,1-diphenylpropan-2-imine

To a screw cap NMR tube was added 8.5 mg (py)$_3$TiCl$_2$ (NPh) (0.1 eq, 0.0191 mmol), aniline (1 eq, 0.191 mmol), 2f (1 eq, 0.191 mmol) and 1 mL of TFT. Initial Time=0 No-D NMR was taken on a Varian INOVA 300 MHz NMR. The NMR tube was then sealed and heated in an oil bath for 16 hours at 110° C. The reaction was cooled to room temperature and No-D NMR was taken.

8b. No-D NMR Hydroamination Reaction of Aniline with 2i (Liu et al., *J. Am. Chem. Soc.* 135:6810-6813 (2013)):

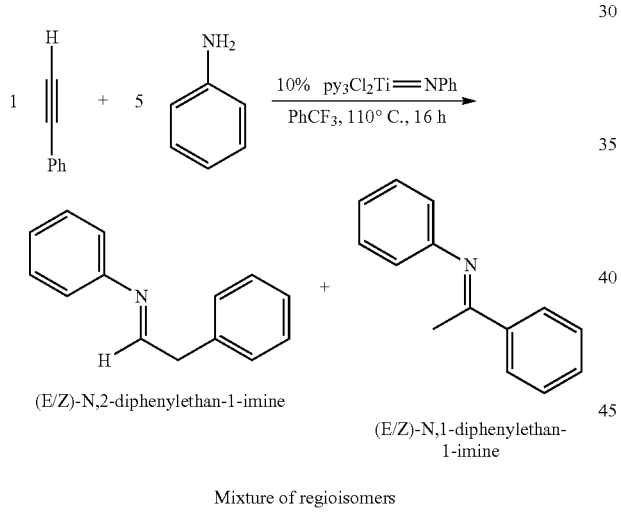

(E/Z)-N,2-diphenylethan-1-imine (E/Z)-N,1-diphenylethan-1-imine

Mixture of regioisomers

To a screw cap NMR tube was added 8.5 mg (py)$_3$TiCl$_2$ (NPh) (0.1 eq, 0.0191 mmol), aniline (5 eq, 0.955 mmol), 2f (1 eq, 0.191 mmol) and 1 mL of TFT. The NMR tube was then sealed and heated in an oil bath for 16 hours at 110° C. After completion of the reaction by No-D NMR the reaction mixture was concentrated and diluted with CDCl$_3$. D$_2$O was then added and the NMR tube was inverted three times before spectra was acquired.

8c. No-D Hydroamination Reaction of Aniline with 2i.

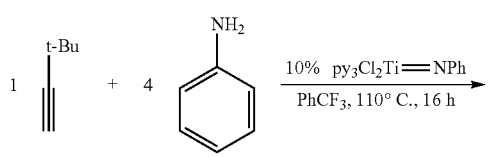

-continued

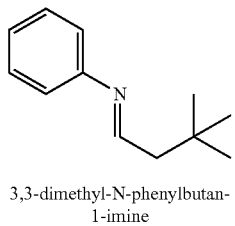

3,3-dimethyl-N-phenylbutan-1-imine

9. Miscellaneous Reactions:
9a. Stoichiometric Reaction of 1b with DIAD (3h).

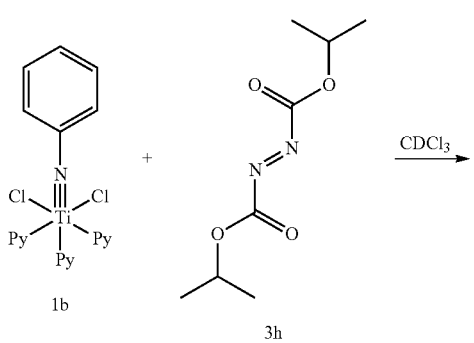

TABLE 5

| Crystal Structure Information for 7: | |
|---|---|
| | 7 |
| CCDC Number | 1037313 |
| Chemical formula | C$_{16}$H$_{30}$Cl$_2$N$_4$Ti |
| Formula weight | 391.08 |
| Crystal system | Trigonal |
| Space group | P3$_1$ |
| a | 11.2050(7) |
| b | 11.2050(7) |
| c | 12.9956(9) |
| α | 90.0 |
| β | 90.0 |
| γ | 120.0 |
| V (Å$^3$) | 1413.03 |
| Z | 3 |
| D$_{calc}$ (g cm$^{-3}$) | 1.379 |
| μ (Mo-K$_α$) (mm$^{-1}$) | 0.742 |
| F(000) | 612 |
| Θ range (°) | 2.62-27.15 |
| Abs. Correction | multi-scan |
| Parameters/restraints | 216/1 |
| wR$_2$ [b] [I > σ2(I)] | 0.0563 |
| R$_1$ [a] | 0.0273 |
| Goodness of fit | 1.001 |

[a] R$_1$ = Σ||F$_o$| − |F$_c$||/Σ|F$_o$|.
[b] wR$_2$ = [Σ[w(F$_o^2$-F$_c^2$)$^2$]/Σ[w(F$_o^2$)$^2$]]$^{1/2}$.

Figure 7:
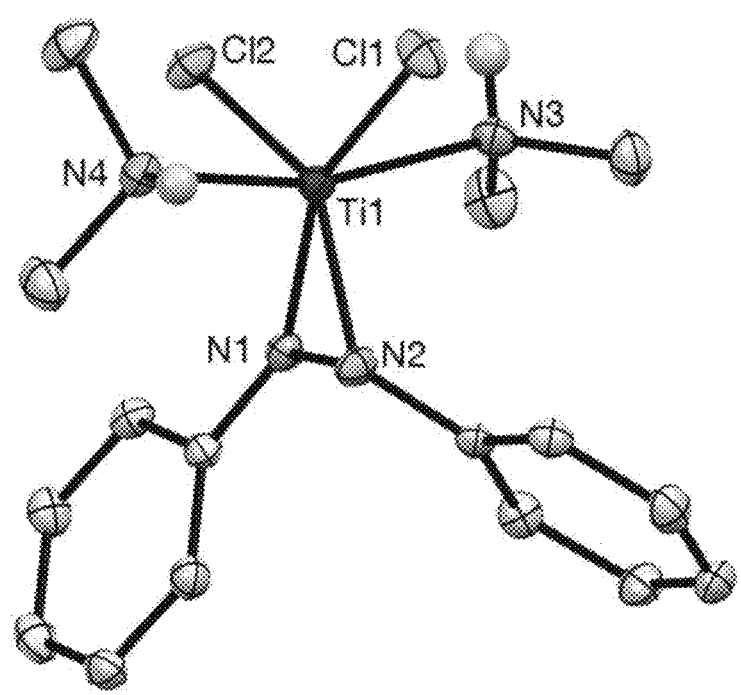
FIG. 7 is a thermal ellipsoid drawing of exemplary compound 7. N1-N2 distance is 1.420(3) Å. Hydrogen atoms omitted for clarity.

The thermal ellipsoid drawing of compound 7 is illustrated in FIG. 7. The N1-N2 distance is 1.420(3) Å. Hydrogen atoms omitted for clarity.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of forming a pyrrole or pyrazole compound the method comprising:

combining at least one compound having a triple bond, at least one azo compound, and at least one Ti(IV) compound under conditions effective for a [2+2+1] cycloaddition reaction to occur and form one or more pyrrole or pyrazole compounds, wherein the at least one Ti(IV) compound is of the formula:

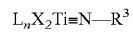  (i)

and/or

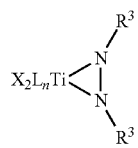  (ii)

wherein:
each $R^3$ independently represents an organic group,
each X independently represents an anionic ligand,
each L independently represents a neutral ligand, and
n=2 to 3.

2. The method of claim 1 wherein each $R^3$ independently represents an alkyl group or an aryl group; each X independently represents an inorganic anionic ligand; and each L independently represents a neutral organic coordinating ligand.

3. The method of claim 1 wherein the at least one azo compound is of the formula $R^3$—N=N—$R^3$, wherein each $R^3$ independently represents an organic group.

4. The method of claim 3 wherein each $R^3$ independently represents an alkyl group or an aryl group.

5. The method of claim 1 wherein the at least one compound having a triple bond is at least one alkyne, and the one or more heterocyclic compounds formed include one or more pyrroles.

6. The method of claim 5 wherein:
the at least one alkyne is of the formula $R^1$—≡—$R^2$, wherein $R^1$ and $R^2$ each independently represent H or an organic group, or $R^1$ and $R^2$ can be combined to form one or more alicyclic and/or aromatic rings; and
the one or more pyrroles formed are of the formulas:

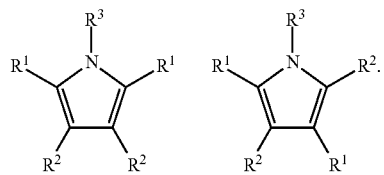

7. The method of claim 6 wherein each $R^3$ independently represents an alkyl group or an aryl group; and each $R^1$ and $R^2$ independently represents hydrogen, an alkyl group, or an aryl group.

8. The method of claim 5 wherein:
the at least one alkyne is of the formula $R^1$—≡—$(CH_2)_y$—≡—$R^2$, wherein $R^1$ and $R^2$ each independently represent H or an organic group, and y=3 to 5; and
the one or more pyrroles formed are of the formula:

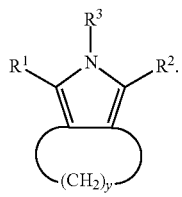

9. The method of claim 8 wherein each $R^3$ independently represents an alkyl group or an aryl group; and each $R^1$ and $R^2$ independently represents hydrogen, an alkyl group, or an aryl group.

10. The method of claim 1 wherein the at least one compound having a triple bond comprises at least one alkyne and at least one nitrile-functional compound, and the one or more compounds formed include one or more pyrazoles.

11. The method of claim 1 wherein:
the at least one alkyne is of the formula $R^1$—≡—$R^2$, wherein $R^1$ and $R^2$ each independently represent H or an organic group, or $R^1$ and $R^2$ can be combined to form one or more alicyclic and/or aromatic rings;
the at least one nitrile-functional compound is of the formula $R^4$—C≡N, wherein $R^4$ represents an organic group; and
the one or more pyrazoles formed are of the formula:

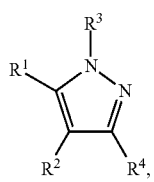

where $R^3$ represents an organic group.

12. The method of claim 11 wherein each $R^3$ independently represents an alkyl group or an aryl group; and each $R^4$ independently represents an alkyl group or an aryl group.

13. The method of claim 1 wherein the at least one Ti(IV) compound is present in catalytic amounts.

14. The method of claim 1 wherein conditions effective comprise the presence of a non-coordinating solvent.

15. The method of claim 1 wherein conditions effective comprise essentially anhydrous conditions.

16. The method of claim 1 wherein conditions effective comprise essentially the absence of oxygen.

* * * * *

UNITED STATES PATENT AND TRADEMARK OFFICE
CERTIFICATE OF CORRECTION

PATENT NO. : 10,065,976 B2
APPLICATION NO. : 14/986928
DATED : September 4, 2018
INVENTOR(S) : Ian A. Tonks and Zachary W. Gilbert Page 1 of 1

It is certified that error appears in the above-identified patent and that said Letters Patent is hereby corrected as shown below:

In the Claims

Column 44 Line 7 In Claim 8, delete "13".

Column 44 Line 54 In Claim 14, delete "effective" and replace with --effectively--.

Column 44 Line 56 In Claim 15, delete "effective" and replace with --effectively--.

Column 44 Line 58 In Claim 16, delete "effective" and replace with --effectively--.

Signed and Sealed this
Twenty-seventh Day of November, 2018

Andrei Iancu
*Director of the United States Patent and Trademark Office*